(12) United States Patent
Asaad et al.

(10) Patent No.: US 9,572,598 B2
(45) Date of Patent: Feb. 21, 2017

(54) UNIPLANAR SURGICAL SCREW ASSEMBLY

(75) Inventors: Wagdy W. Asaad, Burr Ridge, IL (US); Jayson Varghese, Niles, IL (US)

(73) Assignee: Spine Craft, LLc, Westmont, IL (US)

( * ) Notice: Subject to any disclaimer, the term of this patent is extended or adjusted under 35 U.S.C. 154(b) by 924 days.

(21) Appl. No.: 13/570,374

(22) Filed: Aug. 9, 2012

(65) Prior Publication Data

US 2014/0046386 A1 Feb. 13, 2014

(51) Int. Cl.
| | |
|---|---|
| A61B 17/04 | (2006.01) |
| A61B 17/70 | (2006.01) |
| A61B 17/86 | (2006.01) |
| A61B 17/88 | (2006.01) |
| A61B 17/68 | (2006.01) |

(52) U.S. Cl.
CPC ........... *A61B 17/7032* (2013.01); *A61B 17/70* (2013.01); *A61B 17/7002* (2013.01); *A61B 17/708* (2013.01); *A61B 17/7034* (2013.01); *A61B 17/7035* (2013.01); *A61B 17/7037* (2013.01); *A61B 17/7038* (2013.01); *A61B 17/7049* (2013.01); *A61B 17/7079* (2013.01); *A61B 17/7085* (2013.01); *A61B 17/7091* (2013.01); *A61B 17/8605* (2013.01); *A61B 17/88* (2013.01); *A61B 90/03* (2016.02); *A61B 2017/681* (2013.01); *A61B 2090/037* (2016.02)

(58) Field of Classification Search
CPC ......... A61B 17/7032–17/7037; A61B 17/8605
See application file for complete search history.

(56) References Cited

U.S. PATENT DOCUMENTS

| | | |
|---|---|---|
| 5,207,678 A | 5/1993 | Harms et al. |
| 5,360,431 A | 11/1994 | Puno et al. |
| 5,474,555 A | 12/1995 | Puno et al. |
| 5,624,442 A | 4/1997 | Mellinger et al. |
| RE37,665 E | 4/2002 | Ralph et al. |
| 7,144,396 B2 | 12/2006 | Shluzas |
| 7,306,606 B2 | 12/2007 | Sasing |
| 7,338,491 B2 | 3/2008 | Baker et al. |
| 7,682,377 B2 | 3/2010 | Konieczynski et al. |
| 7,722,652 B2 | 5/2010 | Justis et al. |
| 7,727,261 B2 | 6/2010 | Barker et al. |
| 7,766,915 B2 | 8/2010 | Jackson |
| 7,785,354 B2 | 8/2010 | Biedermann et al. |
| 7,867,258 B2 | 1/2011 | Drewry et al. |
| 7,879,075 B2 | 2/2011 | Shluzas |
| 7,896,902 B2 | 3/2011 | Jeon et al. |
| 7,901,435 B2 | 3/2011 | Slivka et al. |
| 7,942,909 B2 | 5/2011 | Hammill, Sr. et al. |
| 7,951,173 B2 | 5/2011 | Hammill, Sr. et al. |
| 7,955,363 B2 | 6/2011 | Richelsoph |

(Continued)

OTHER PUBLICATIONS

APEX Spine System Vertebral Body Derotation Surgical Technique, Jun. 2012.

*Primary Examiner* — Matthew Lawson
(74) *Attorney, Agent, or Firm* — Law Office of Alan W. Cannon

(57) ABSTRACT

Uniplanar surgical screw assemblies described include: a fastener including an elongate shaft; a saddle-shaped tulip having a tulip having a bore therethrough dimensioned to allow the distal end of the elongate shaft to pass therethrough, but to prevent passage of the head therethrough; and one or more features for limiting angular movement of the shaft, relative to the tulip, to one plane.

29 Claims, 11 Drawing Sheets

(56) References Cited

U.S. PATENT DOCUMENTS

| | | |
|---|---|---|
| 7,967,849 B2 | 6/2011 | Carson et al. |
| 8,021,397 B2 | 9/2011 | Farris et al. |
| 8,057,519 B2 | 11/2011 | Justis et al. |
| 8,075,603 B2 | 12/2011 | Hammill, Sr. et al. |
| 8,080,036 B2 | 12/2011 | Shim et al. |
| 8,088,152 B2 | 1/2012 | Schumacher |
| 8,128,667 B2 | 3/2012 | Jackson |
| 8,137,387 B2 | 3/2012 | Garamszegi |
| 8,162,989 B2 | 4/2012 | Khalili |
| 8,167,910 B2 | 5/2012 | Nilsson |
| 2005/0261687 A1* | 11/2005 | Garamszegi et al. .......... 606/61 |
| 2007/0049933 A1 | 3/2007 | Ahn et al. |
| 2008/0147129 A1* | 6/2008 | Biedermann ...... A61B 17/7032 606/308 |
| 2008/0234757 A1 | 9/2008 | Jacofsky et al. |
| 2009/0105769 A1* | 4/2009 | Rock et al. .................. 606/308 |
| 2009/0105771 A1 | 4/2009 | Lei et al. |
| 2010/0094343 A1 | 4/2010 | Pham et al. |
| 2010/0145394 A1 | 6/2010 | Harvey et al. |
| 2010/0204735 A1 | 8/2010 | Gephart et al. |
| 2010/0211114 A1* | 8/2010 | Jackson ........................ 606/302 |
| 2010/0305621 A1* | 12/2010 | Wang et al. ................. 606/305 |
| 2011/0172718 A1* | 7/2011 | Felix ................. A61B 17/7032 606/305 |
| 2011/0178558 A1 | 7/2011 | Barry |

\* cited by examiner

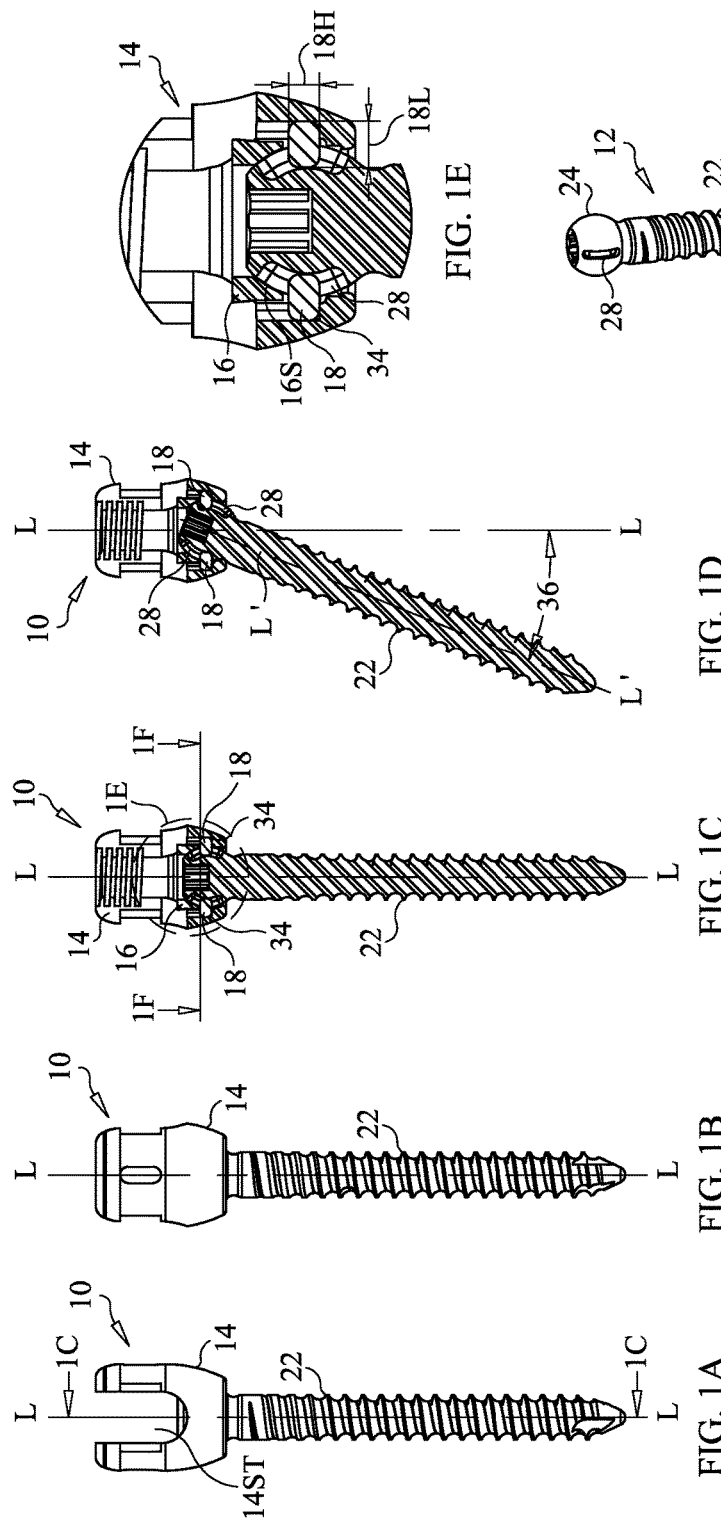

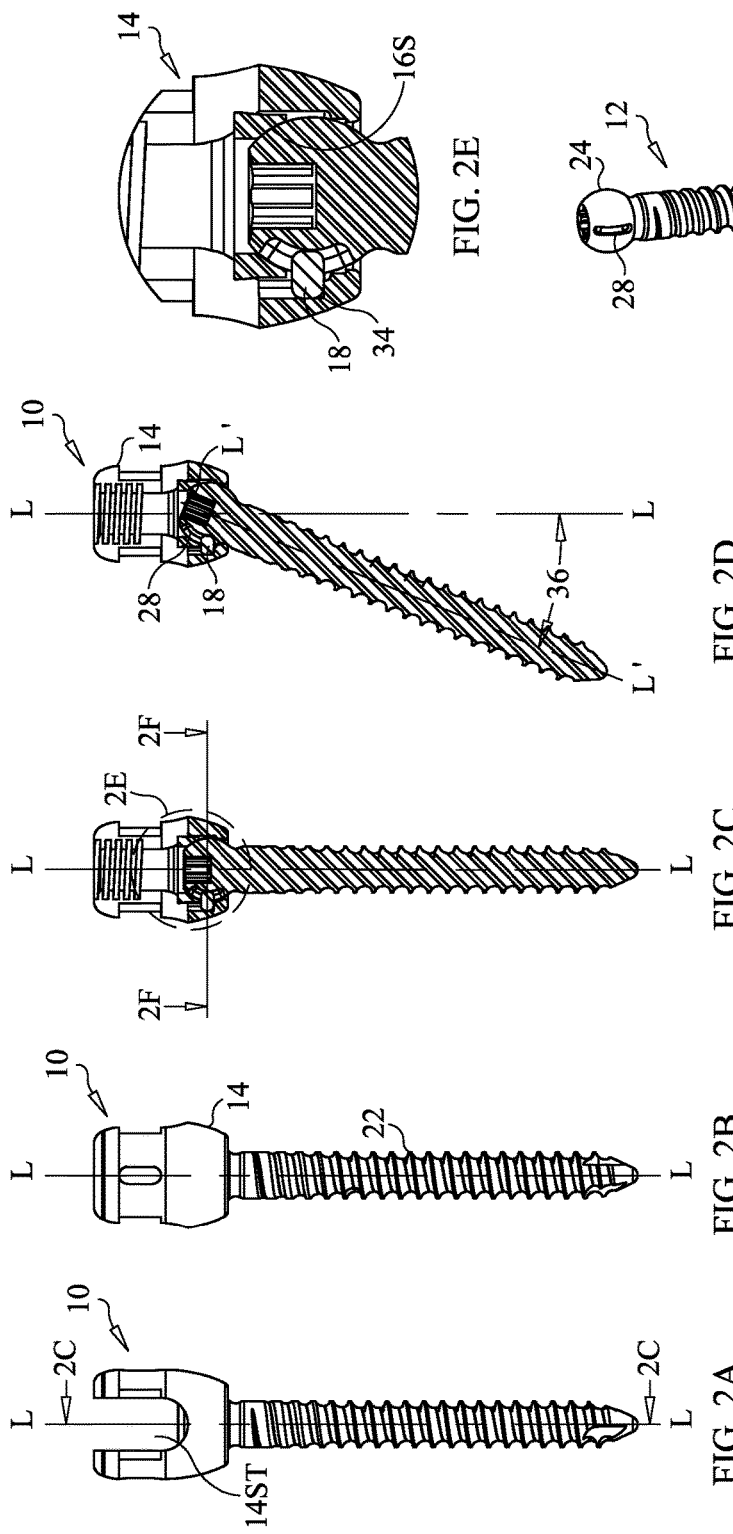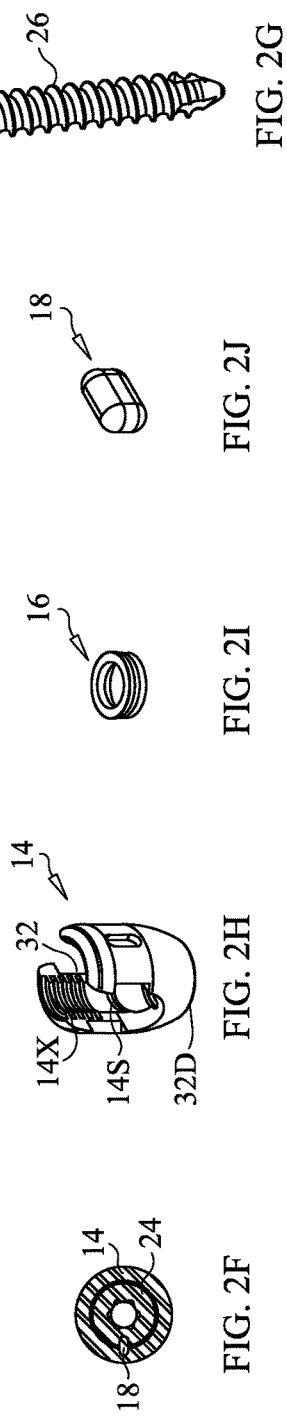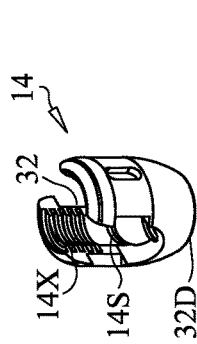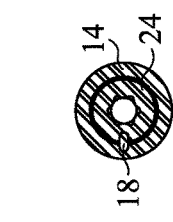

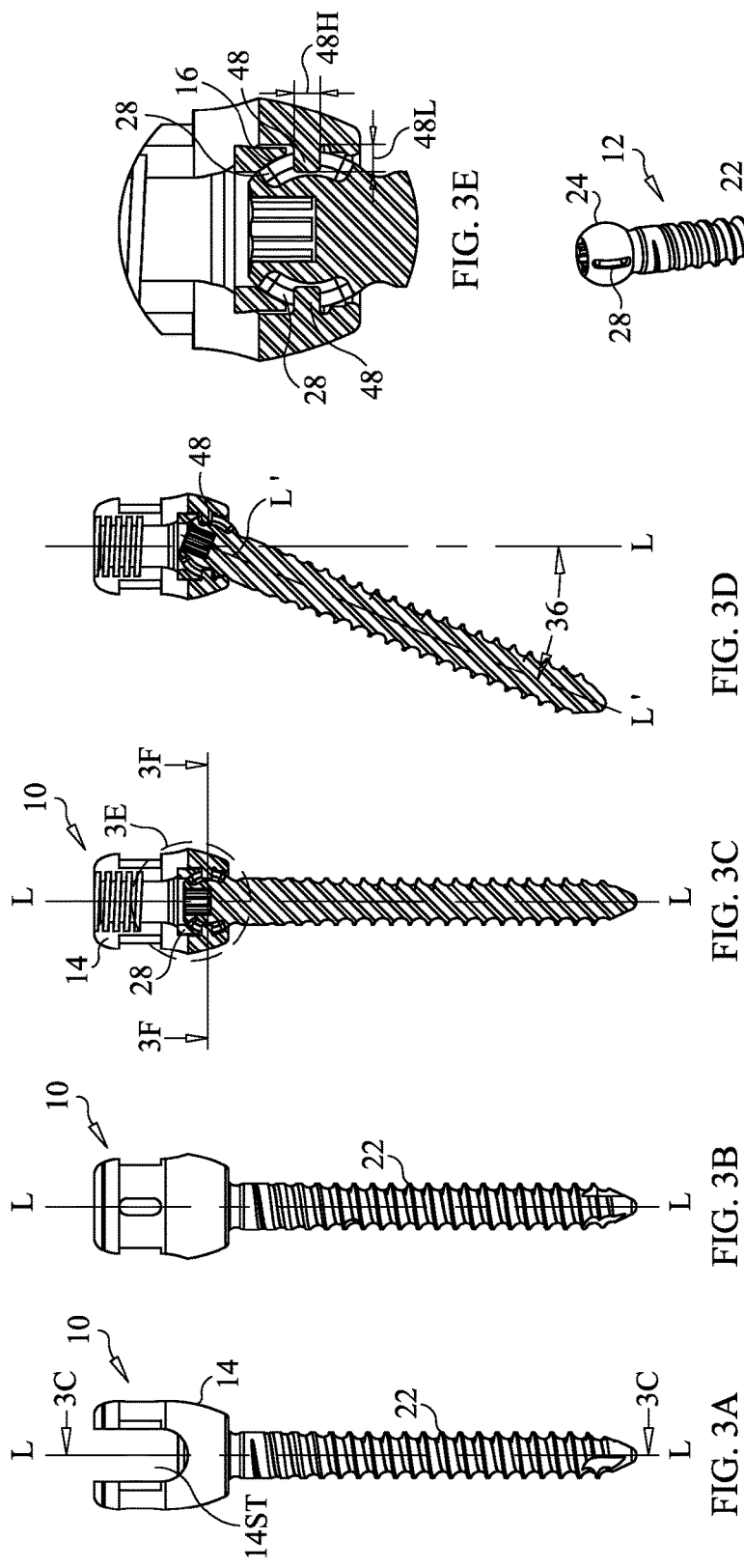

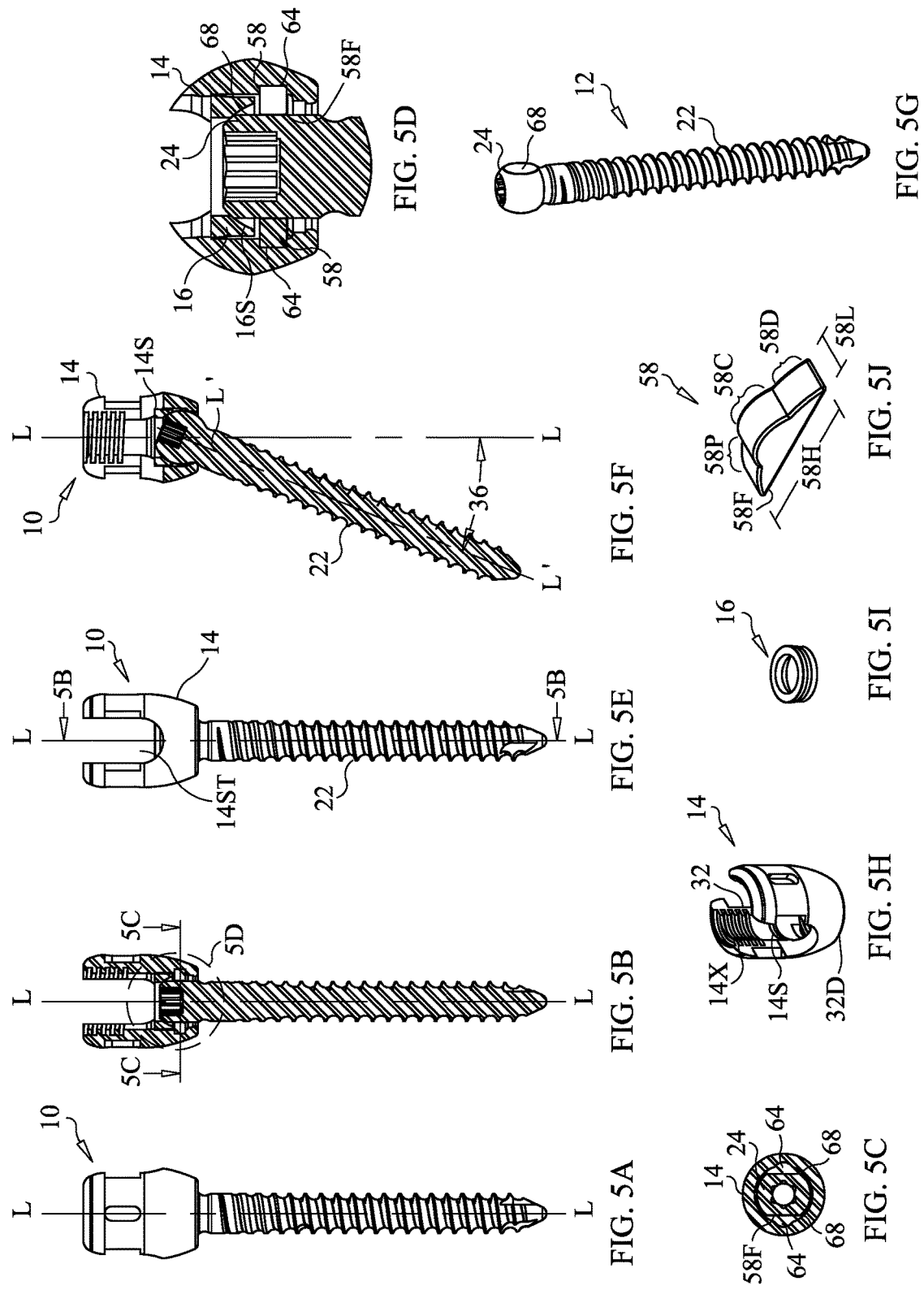

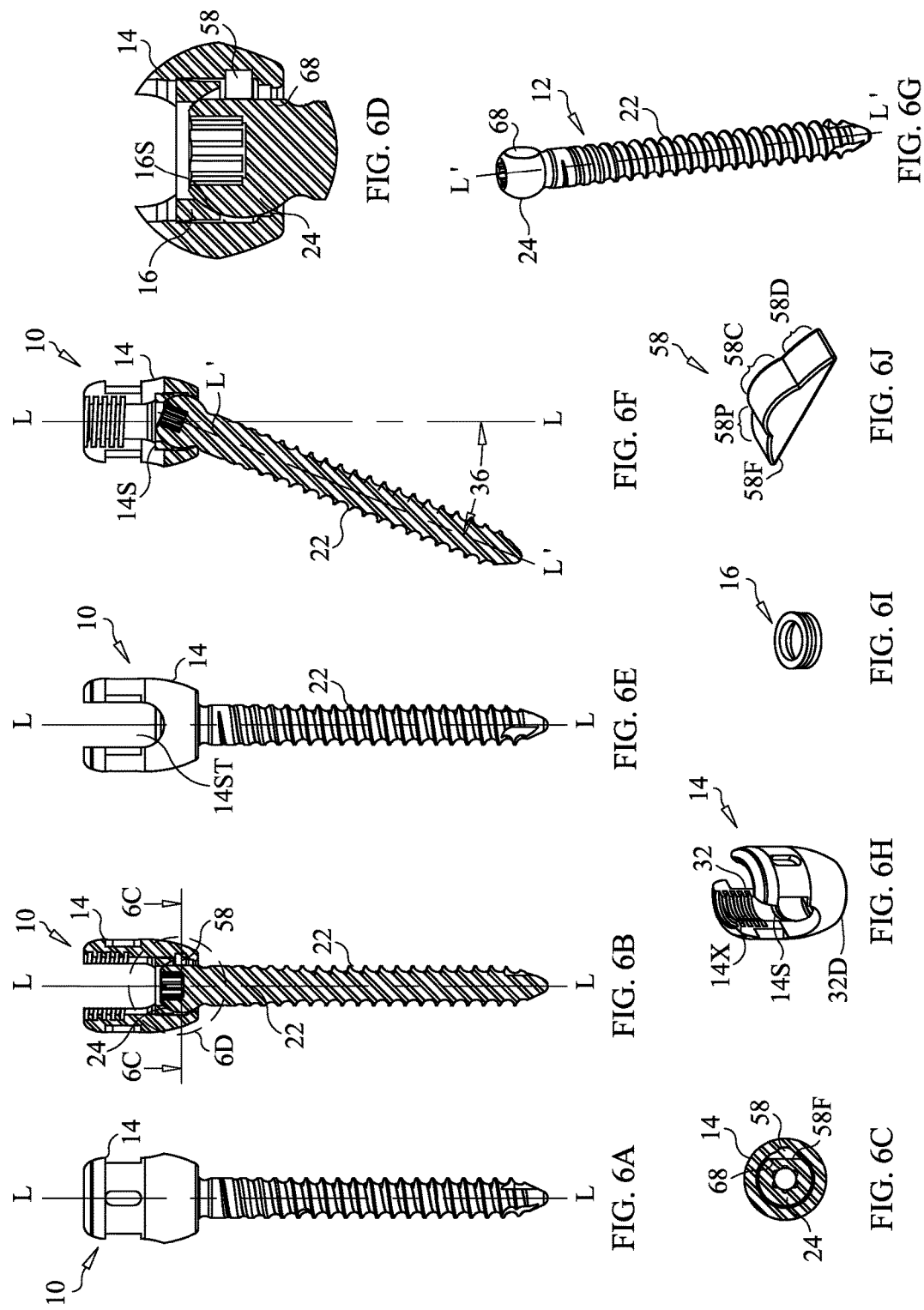

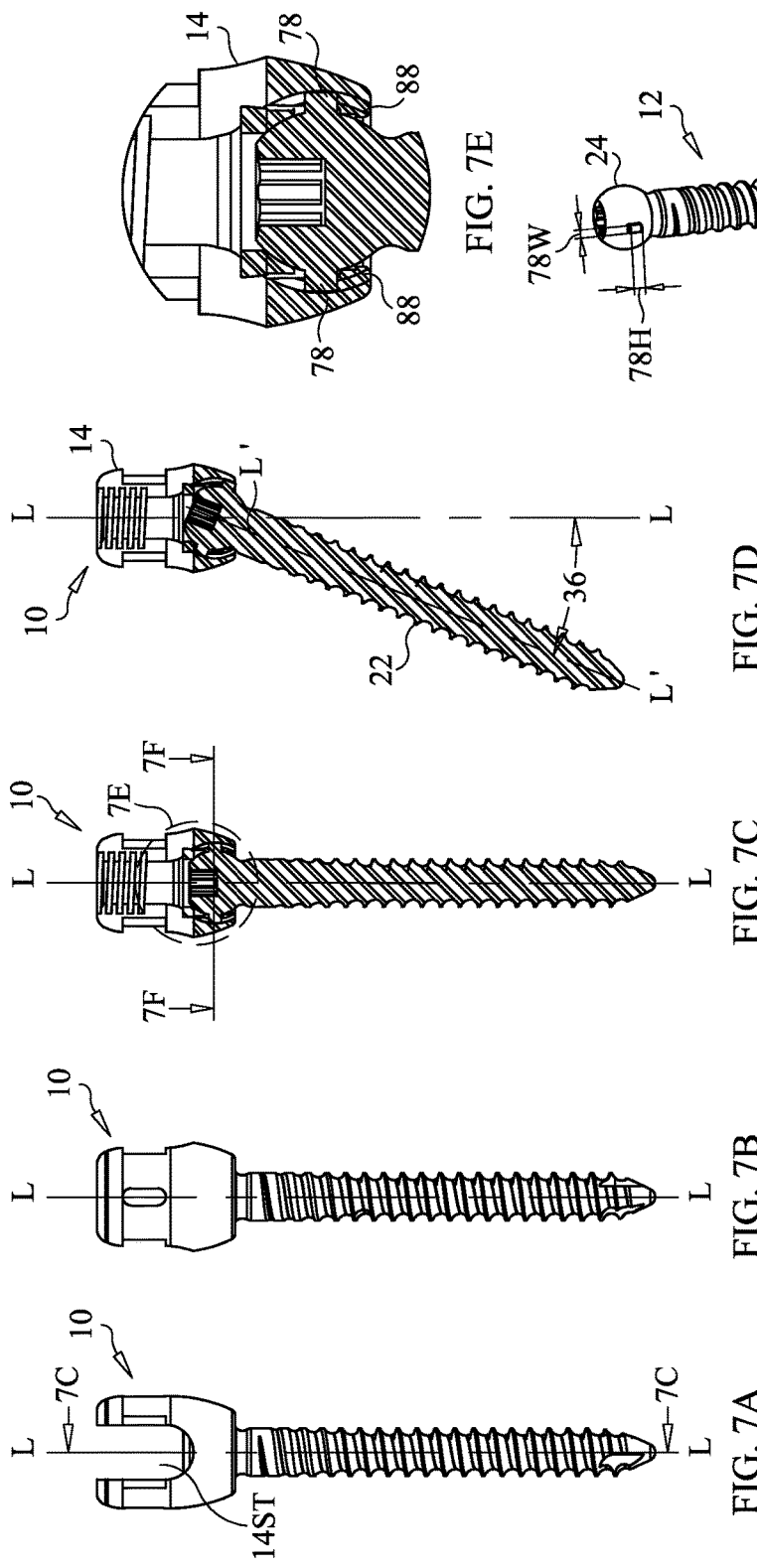

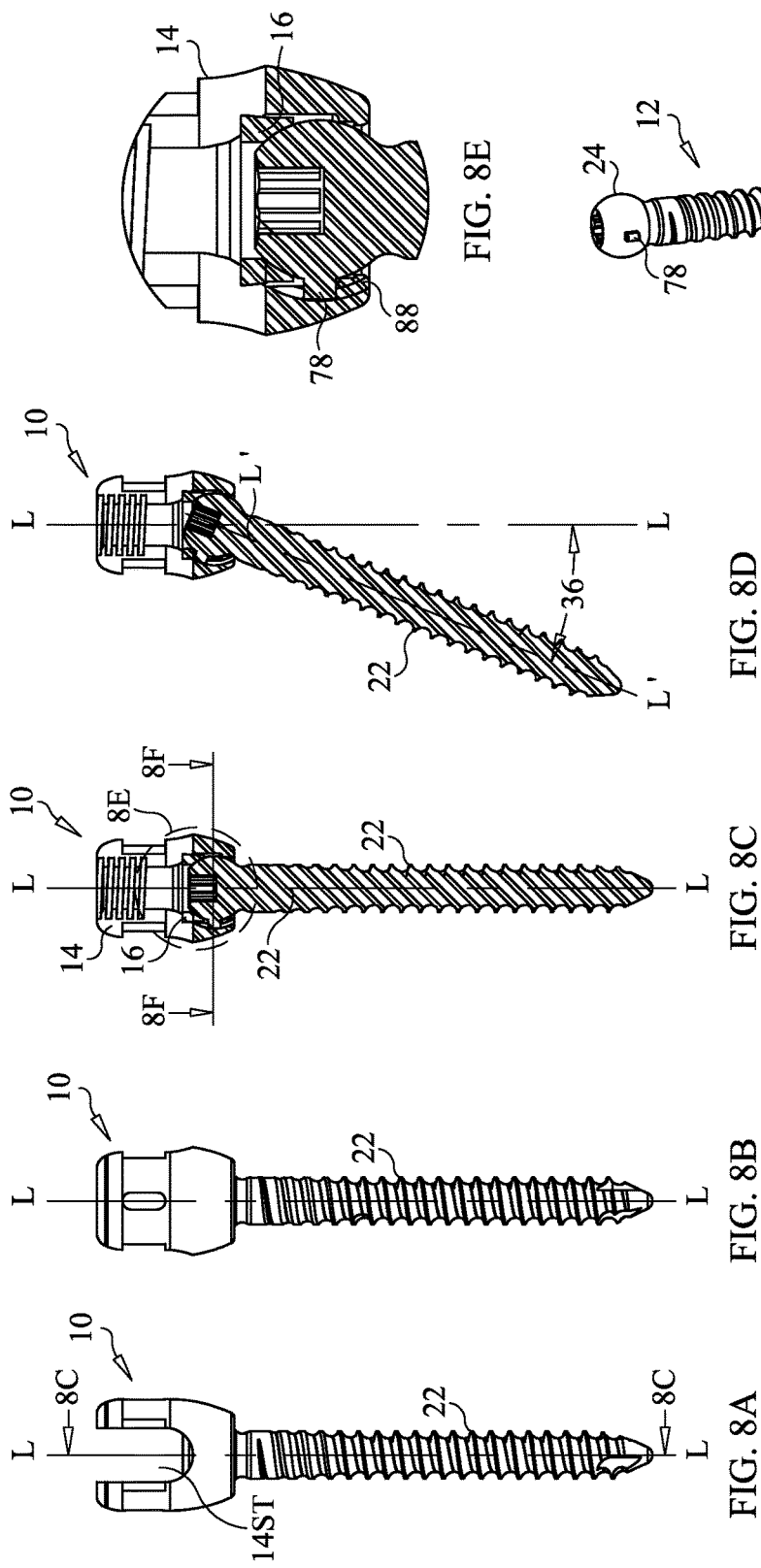

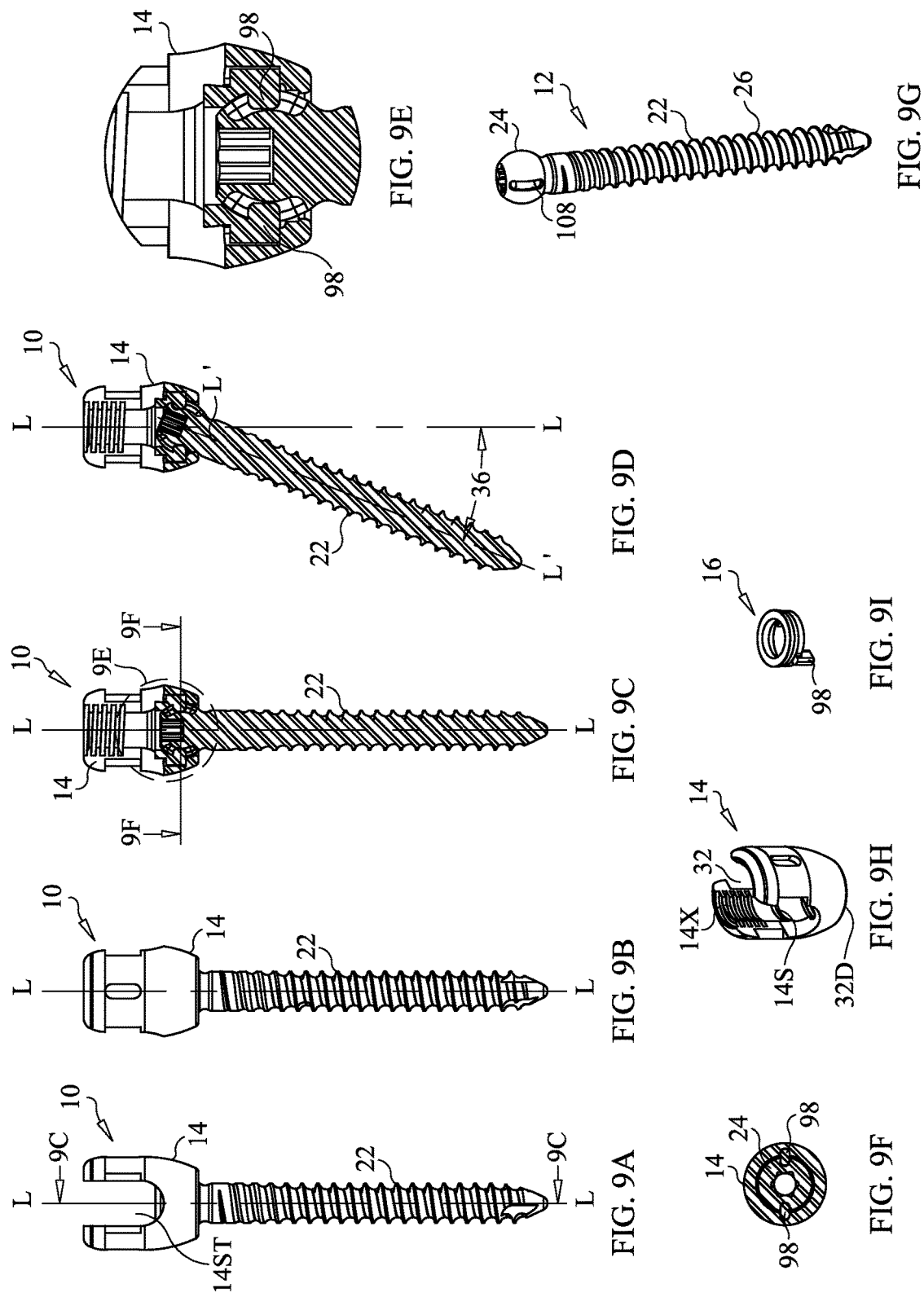

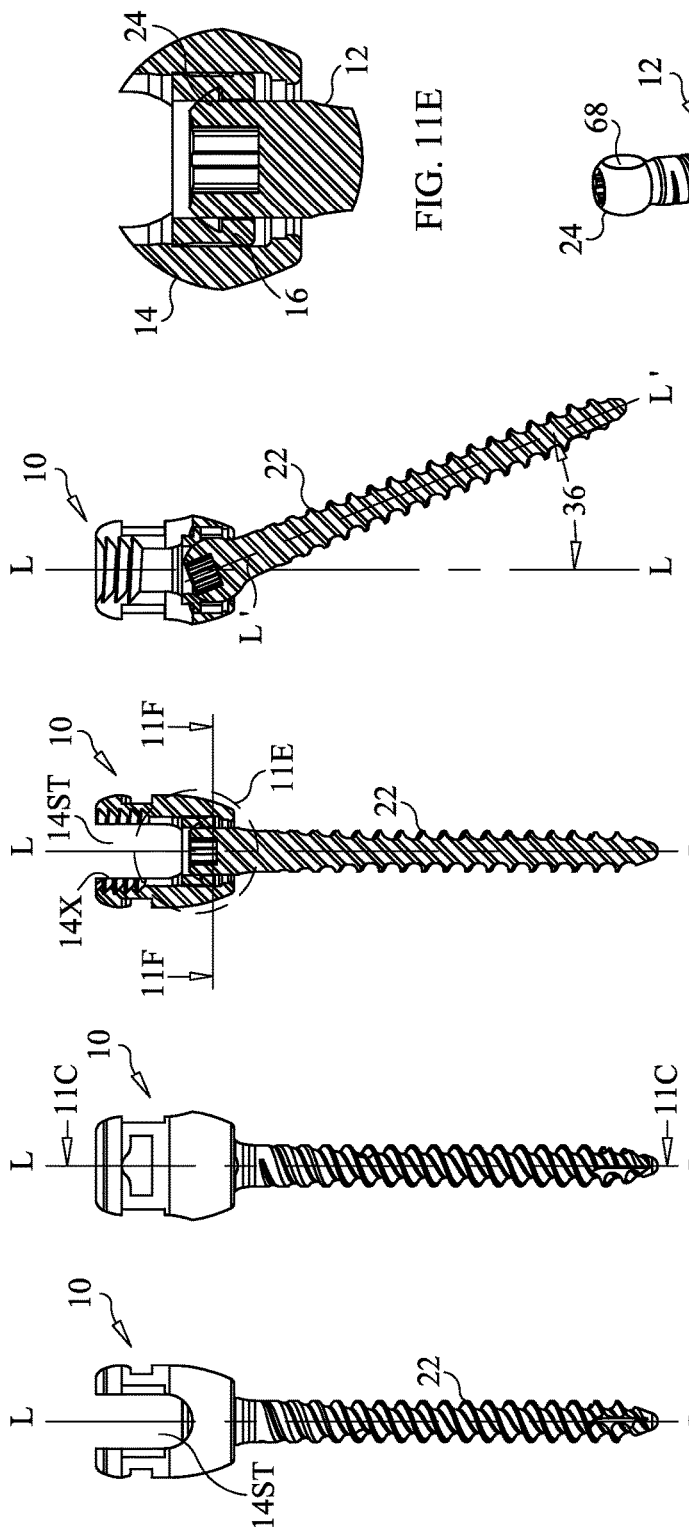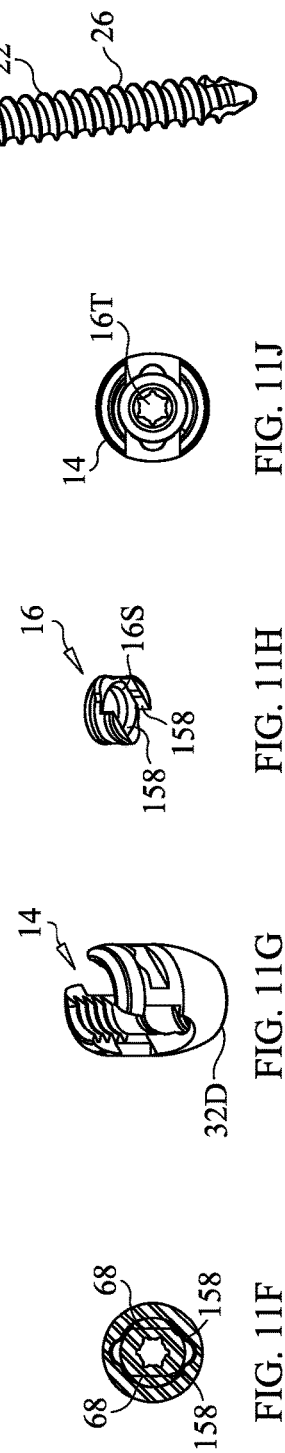

UNIPLANAR SURGICAL SCREW ASSEMBLY

FIELD OF THE INVENTION

The present invention relates to the field of orthopedic surgery, in particular to devices, systems and assemblies for stabilizing and/or fixing bones and/or joints in a patient. More particularly, the present invention a uniplanar, surgical attachment device that alternatively permits uniplanar pivoting or no pivoting at all.

BACKGROUND OF THE INVENTION

The fixation and/or stabilization of bones and/or bone fragments is commonly required by orthopedic surgeons to treat injuries such as fractures or disease. To accomplish this, the bones/bone fragments can be joined by a rod, plate or the like, which is fixed to the bones/bone fragments via fasteners such as screws, pins or the like. The connection by the rod(s), plate(s) or the like maintains the bones/bone fragments in a desired orientation and/or at desired spacings, positions, etc. Different situations often require the adjustment of such spacings or orientations, or the removal of the apparatus, sometimes with replacement by another apparatus. For these reasons it is useful to provide fasteners that can be fixed or released, and can also articulate to adjust relative to the rod, plate, or the like, as required by the arrangement of the bones/bone fragments being treated.

In spinal surgery, it is often necessary to secure various implants to the vertebrae and interconnect the vertebrae by attaching one or more rods or plates to the implants. Due to the complex curvature of the spine, as well as irregularities of the same that often need to be treated, it is often difficult to align a rod or plate with all of the implants/fasteners fixed to the various vertebrae to be connected via the rod or plate. By providing fasteners that have some articulation ability, this allows more flexibility in joining the fasteners (and thus the vertebrae that they are attached to) to a rod or plate in the orientations needed.

In some surgeries, it is necessary to span multiple vertebrae of the spine with rods that provide stabilizing forces to the vertebrae to help maintain the desired orientations of the vertebrae to maintain a desired curvature in the spine. In these instances, uniplanar fasteners that allow pivoting in only one plane can be useful, as opposed to the more commonly used polyaxial screws, as polyaxial screws may be more likely to fail by rotating rather than withstanding a lateral force applied to the rod therethrough.

There is a continuing need for improved uniplanar fasteners for use in surgical orthopedics procedures where limitation of articulation of the fasteners to only one plane is advantageous to the needs for joining bones, bone fragments and/or joints.

There is a continuing need for improved uniplanar fasteners for use in surgical orthopedics procedures where limitation of articulation of the fasteners to only one plane is advantageous to the needs for joining bones, bone fragments and/or joints, which uniplanar fasteners can alternatively be set to allow uniplanar articulation, or to prevent all articulation and lock the fastener in a desired configuration.

SUMMARY OF THE INVENTION

In one aspect of the present invention, a uniplanar surgical screw is provided that includes: a fastener including an elongate shaft having a proximal end and a distal end and a head at the proximal end, the head having an external surface; a saddle-shaped tulip having a tulip proximal end, a tulip distal end, an external surface and an internal bearing surface, the tulip distal end having a bore therethrough dimensioned to allow the distal end of the elongate shaft to pass therethrough, but to prevent passage of the head therethrough; a slot formed in one of the external surface of the head or the internal bearing surface of the tulip and extending in a proximal-distal direction; and a protrusion extending from the other of the external surface of the head or the internal bearing surface of the tulip, the protrusion being configured and dimensioned to be received within the slot and to slide in the slot, relative to the slot; wherein the slot and the protrusion permit the fastener to move relative to the tulip in only one plane.

In at least one embodiment, the slot is formed in the external surface of the head.

In at least one embodiment, the protrusion comprises an insert fitted in a recess in the internal bearing surface of the tulip.

In at least one embodiment, the slot is formed in the internal bearing surface of the tulip.

In at least one embodiment, the protrusion is fixed relative to the head.

In at least one embodiment, the protrusion is integral with the head.

In at least one embodiment, the slot comprises a pair of slots aligned diametrically opposite one another in one of the external surface of the head or the internal bearing surface of the tulip, each the slot extending in a proximal-distal direction; and the protrusion comprises a pair of protrusions extending from the other of the external surface of the head or the internal bearing surface of the tulip, the protrusions being configured and dimensioned to be received within the slots and to slide in the slots, relative to the slots, respectively.

In at least one embodiment, the assembly includes a saddle, the saddle being configured and dimensioned to be fitted in the tulip against the head of the fastener to prevent the head from moving proximally relative to the tulip.

In at least one embodiment, the saddle is configured to apply compression to the head to lock an orientation of the fastener relative to the tulip, thereby preventing the movement in one plane.

In at least one embodiment, a saddle is provided that is configured and dimensioned to be fitted in the tulip against the head of the fastener to prevent the head from moving proximally relative to the tulip; the saddle including a notch configured to allow translation of the protrusion.

In another aspect of the present invention, a uniplanar surgical screw assembly is provided that includes: a fastener including an elongate shaft having a proximal end and a distal end and a head at said proximal end, the head having a flat surface formed on an external surface having otherwise substantially spherical curvature; a saddle-shaped tulip having a tulip proximal end, a tulip distal end, an external surface and an internal bearing surface having substantially spherical curvature configured to permit articulation of a curved portion of said external surface of the head thereagainst, and the tulip distal end having a bore therethrough dimensioned to allow the distal end of the elongate shaft to pass therethrough, but to prevent passage of the head therethrough; and an interface component having a flat interface surface; wherein, when the assembly is assembled, the flat interface surface interfaces with the flat surface of the head, thereby permitting the fastener to move relative to the tulip in only one plane.

In at least one embodiment, the flat surface on the head comprises a pair of flat surfaces formed diametrically opposite one another on the head; and the flat interface surface comprises a pair of flat interface surfaces configured to interface with the pair of flat surfaces, respectively.

In at least one embodiment, the interface component comprises a saddle, the saddle being configured and dimensioned to be fitted in the tulip against the head of the fastener to prevent the head from moving proximally relative to the tulip.

In at least one embodiment, the saddle is configured to apply compression to the head to lock an orientation of the fastener relative to the tulip, thereby preventing movement in the one plane in addition to preventing movement in all other planes.

In at least one embodiment, the saddle-shaped tulip comprises a recess formed in the internal bearing surface and the interface component comprises an insert having the flat interface surface and a non-flat side, the non-flat side configured and dimensioned to be received in the recess; and wherein, when the insert is received in the recess and the head is received in the tulip, the flat interface surface of the insert interfaces with the flat surface of the head, thereby permitting the fastener to move relative to the tulip in only one plane.

In at least one embodiment, the recess comprises a pair of recesses formed in the internal bearing surface at diametrically opposite locations, and the insert comprises a pair of the inserts configured and dimensioned to be received in the recesses, respectively.

In at least one embodiment, the assembly includes a saddle, the saddle being configured and dimensioned to be fitted in the tulip against the head of the fastener to prevent the head from moving proximally relative to the tulip.

In at least one embodiment, the saddle is configured to apply compression to the head to lock an orientation of the fastener relative to the tulip, thereby preventing the movement in one plane.

In at least one embodiment, the non-flat side comprise a bulbous portion extending further from the flat side than an extent to which a remainder of the non-flat side extends from the flat side.

In at least one embodiment, the non-flat side is shaped and configured to prevent the insert from sliding relative to the recess.

In at least one embodiment, the non-flat side comprises a proximal end portion, a central portion, and a distal end portion, wherein the central portion extends further from the flat side than the distances by which the proximal and distal end portions extend from the flat side.

In at least one embodiment, the non-flat side comprises a proximal end portion, a central portion, and a distal end portion, wherein the central portion has a first curvature and the proximal and distal end portions have a second curvature, the first curvature having a smaller radius of curvature than the second curvature.

In another aspect of the present invention, a uniplanar surgical screw assembly is provided that includes: a fastener including an elongate shaft having a proximal end and a distal end and a head at the proximal end, the head having an external surface; a saddle-shaped tulip having a tulip proximal end, a tulip distal end, an external surface and an internal bearing surface, the tulip distal end having a bore therethrough dimensioned to allow the distal end of the elongate shaft to pass therethrough, but to prevent passage of the head therethrough; a saddle, the saddle being configured and dimensioned to be fitted in the tulip against the head of the fastener to prevent the head from moving proximally relative to the tulip, the saddle having an internal surface configured to interface with the external surface of the head; a slot formed in one of the external surface of the head or the internal surface of the saddle and extending in a proximal-distal direction; and a protrusion extending from the other of the external surface of the head or the internal surface of the saddle, the protrusion being configured and dimensioned to be received within the slot and to slide in the slot, relative to the slot; wherein the slot and the protrusion permit the fastener to move relative to the tulip in only one plane.

In at least one embodiment, the protrusion extends from the internal surface of the saddle.

In at least one embodiment, the protrusion is integrally formed with the internal surface of the saddle.

In at least one embodiment, the slot is formed in the external surface of the head.

In at least one embodiment, the protrusion is fixed relative to the saddle.

In at least one embodiment, the slot comprises a pair of slots aligned diametrically opposite one another in one of the external surface of the head or the internal surface of the saddle, each the slot extending in the proximal-distal direction; and the protrusion comprises a pair of protrusions extending from the other of the external surface of the head or the internal surface of the saddle, the protrusions being configured and dimensioned to be received within the slots and to slide in the slots, relative to the slots, respectively.

In at least one embodiment, the saddle is configured to apply compression to the head to lock an orientation of the fastener relative to the tulip, thereby preventing the movement in one plane.

These and other features of the invention will become apparent to those persons skilled in the art upon reading the details of the assemblies, components and systems as more fully described below.

BRIEF DESCRIPTION OF THE DRAWINGS

FIG. 1A is a plan view of a uniplanar surgical screw assembly according to an embodiment of the present invention.

FIG. 1B shows the assembly of FIG. 1A having been rotated about its longitudinal axis L-L by ninety degrees, relative to the view shown in FIG. 1A.

FIG. 1C is a longitudinal sectional view of the embodiment of FIG. 1A taken along line 1C-1C.

FIG. 1D shows the assembly of FIG. 1C, after pivoting the shaft relative to the tulip.

FIG. 1E is an enlarged detailed view of the portion of FIG. 1C within circle 1E.

FIG. 1F is a cross sectional view of the assembly taken along line 1F-1F in FIG. 1C.

FIG. 1G is an isolated, perspective view of the tulip component of FIG. 1A.

FIG. 1H is an isolated, perspective view of the saddle component of FIG. 1A.

FIG. 1I is an isolated, perspective view of an insert component of FIG. 1A.

FIG. 1J is an isolated, perspective view of the fastener component of FIG. 1A.

FIG. 2A is a plan view of a uniplanar surgical screw assembly according to another embodiment of the present invention.

FIG. 2B shows the assembly of FIG. 2A having been rotated about its longitudinal axis L-L by ninety degrees, relative to the view shown in FIG. 2A.

FIG. 2C is a longitudinal sectional view of the embodiment of FIG. 2A taken along line 2C-2C.

FIG. 2D shows the assembly of FIG. 2C, after pivoting the shaft relative to the tulip.

FIG. 2E is an enlarged detailed view of the portion of FIG. 2C within circle 2E.

FIG. 2F is a cross sectional view of the assembly taken along line 2F-2F in FIG. 2C.

FIG. 2G is an isolated, perspective view of the fastener of FIG. 2A.

FIG. 2H is an isolated, perspective view of the tulip component of FIG. 2A.

FIG. 2I is an isolated, perspective view of the saddle component of FIG. 2A.

FIG. 2J is an isolated, perspective view of the insert component of FIG. 2A.

FIG. 3A is a plan view of a uniplanar surgical screw assembly according to another embodiment of the present invention.

FIG. 3B shows the assembly of FIG. 3A having been rotated about its longitudinal axis L-L by ninety degrees, relative to the view shown in FIG. 3A.

FIG. 3C is a longitudinal sectional view of the embodiment of FIG. 3A taken along line 3C-3C.

FIG. 3D shows the assembly of FIG. 3C, after pivoting the shaft relative to the tulip.

FIG. 3E is an enlarged detailed view of the portion of FIG. 3C within circle 3E.

FIG. 3F is a cross sectional view of the assembly taken along line 3F-3F in FIG. 3C.

FIG. 3G is an isolated, perspective view of the fastener of FIG. 3A.

FIG. 3H is an isolated, perspective view of the tulip component of FIG. 3A.

FIG. 3I is an isolated, perspective view of the saddle component of FIG. 3A.

FIG. 5A is a plan view of a uniplanar surgical screw assembly according to another embodiment of the present invention.

FIG. 5B is a longitudinal sectional view of the embodiment of FIG. 5E taken along line 5B-5B.

FIG. 5C is a cross sectional view of the assembly taken along line 5C-5C in FIG. 5B.

FIG. 5D is an enlarged detailed view of the portion of FIG. 5B within circle 5D.

FIG. 5E shows the assembly of FIG. 5A having been rotated about its longitudinal axis L-L by ninety degrees, relative to the view shown in FIG. 5A.

FIG. 5F shows the assembly of FIG. 5B, after pivoting the shaft relative to the tulip.

FIG. 5G is an isolated, perspective view of the fastener of FIG. 5A.

FIG. 5H is an isolated, perspective view of the tulip component of FIG. 5A.

FIG. 5I is an isolated, perspective view of the saddle component of FIG. 5A.

FIG. 5J is an isolated, perspective view of a flat insert component of FIG. 5A.

FIG. 6A is a plan view of a uniplanar surgical screw assembly according to another embodiment of the present invention.

FIG. 6B is a longitudinal sectional view of the embodiment of FIG. 6E taken along line 6B-6B.

FIG. 6C is a cross sectional view of the assembly taken along line 6C-6C in FIG. 6B.

FIG. 6D is an enlarged detailed view of the portion of FIG. 6B within circle 6D.

FIG. 6E shows the assembly of FIG. 6A having been rotated about its longitudinal axis L-L by ninety degrees, relative to the view shown in FIG. 6A.

FIG. 6F shows the assembly of FIG. 6B, after pivoting the shaft relative to the tulip.

FIG. 6G is an isolated, perspective view of the fastener of FIG. 6A.

FIG. 6H is an isolated, perspective view of the tulip component of FIG. 6A.

FIG. 6I is an isolated, perspective view of the saddle component of FIG. 6A.

FIG. 6J is an isolated, perspective view of the flat insert component of FIG. 6A.

FIG. 7A is a plan view of a uniplanar surgical screw assembly according to another embodiment of the present invention.

FIG. 7B shows the assembly of FIG. 7A having been rotated about its longitudinal axis L-L by ninety degrees, relative to the view shown in FIG. 7A.

FIG. 7C is a longitudinal sectional view of the embodiment of FIG. 7A taken along line 7C-7C.

FIG. 7D shows the assembly of FIG. 7C, after pivoting the shaft relative to the tulip.

FIG. 7E is an enlarged detailed view of the portion of FIG. 7C within circle 7E.

FIG. 7F is a cross sectional view of the assembly taken along line 7F-7F in FIG. 7C.

FIG. 7G is an isolated, perspective view of the fastener of FIG. 7A.

FIG. 7H is an isolated, perspective view of the tulip component of FIG. 7A.

FIG. 7I is an isolated, perspective view of the saddle component of FIG. 7A.

FIG. 8A is a plan view of a uniplanar surgical screw assembly according to another embodiment of the present invention.

FIG. 8B shows the assembly of FIG. 8A having been rotated about its longitudinal axis L-L by ninety degrees, relative to the view shown in FIG. 8A.

FIG. 8C is a longitudinal sectional view of the embodiment of FIG. 8A taken along line 8C-8C.

FIG. 8D shows the assembly of FIG. 8C, after pivoting the shaft relative to the tulip.

FIG. 8E is an enlarged detailed view of the portion of FIG. 8C within circle 8E.

FIG. 8F is a cross sectional view of the assembly taken along line 8F-8F in FIG. 8C.

FIG. 8G is an isolated, perspective view of the fastener of FIG. 8A.

FIG. 8H is an isolated, perspective view of the tulip component of FIG. 8A.

FIG. 8I is an isolated, perspective view of the saddle component of FIG. 8A.

FIG. 9A is a plan view of a uniplanar surgical screw assembly according to another embodiment of the present invention.

FIG. 9B shows the assembly of FIG. 9A having been rotated about its longitudinal axis L-L by ninety degrees, relative to the view shown in FIG. 9A.

FIG. 9C is a longitudinal sectional view of the embodiment of FIG. 9A taken along line 9C-9C.

FIG. 9D shows the assembly of FIG. 9C, after pivoting the shaft relative to the tulip.

FIG. 9E is an enlarged detailed view of the portion of FIG. 9C within circle 9E.

FIG. 9F is a cross sectional view of the assembly taken along line 9F-9F in FIG. 9C.

FIG. 9G is an isolated, perspective view of the fastener of FIG. 9A.

FIG. 9H is an isolated, perspective view of the tulip component of FIG. 9A.

FIG. 9I is an isolated, perspective view of the saddle component of FIG. 9A.

FIG. 11A is a plan view of a uniplanar surgical screw assembly according to another embodiment of the present invention.

FIG. 11B is a view of the embodiment of FIG. 11A after rotation about the longitudinal axis by ninety degrees.

FIG. 11C is a longitudinal sectional view of the embodiment of FIG. 11B taken along line 11C-11C.

FIG. 11D is a view showing the fastener angled relative to the tulip, according to an embodiment of the present invention.

FIG. 11E is an enlarged detailed view of the portion of FIG. 11C within circle 11E.

FIG. 11F is a cross-sectional view of the assembly taken along line 11F-11F in FIG. 11C FIG. 11G is an isolated, perspective view of the tulip component of FIGS. 11A-11F.

FIG. 11H is an isolated, perspective view of the saddle component of FIGS. 11A-11F.

FIG. 11I is an isolated, perspective view of the fastener component of FIGS. 11A-11F.

FIG. 11J is a proximal end view of FIG. 11B.

DETAILED DESCRIPTION OF THE INVENTION

Figure 4E:
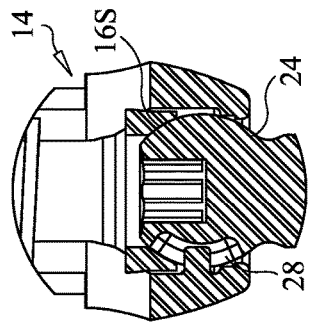
FIG. 4E is an enlarged detailed view of the portion of FIG. 4C within circle 4E.

Before the present assemblies, components and systems are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a protrusion" includes a plurality of such protrusions and reference to "the screw" includes reference to one or more screws and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The embodiments described below are directed to uniplanar screw assemblies for use with an orthopedic rod. Although the following description is related to such use with an orthopedic rod, for example for surgical procedures treating the spine, it is noted that the present invention as described can be used in other applicable surgical procedures, such as in other orthopedic procedures for fixing and/or aligning bones, joints, etc. Furthermore, although the specific embodiments shown in the figures and described below employ a screw as a fastener, it should be understood that other types of fasteners or securing elements may alternatively or additionally be used, including, but not limited to lamina hooks, sacral blocks, etc.

Referring now to FIG. 1A, a plan view of a uniplanar surgical screw assembly 10 is shown, according to an embodiment of the present invention. FIG. 1B shows assembly 10 having been rotated about its longitudinal axis L-L by ninety degrees, relative to the view shown in FIG. 1A. The assembly 10 of the embodiment of FIGS. 1A-1J includes a fastener 12 (see the isolated view of FIG. 1J), a saddle-shaped tulip 14 (see the isolated view of FIG. 1G), a saddle 16 (see the isolated view of FIG. 1H) and a pair of inserts 18 (see isolated view of an insert 18 in FIG. 1I).

Fastener 12 includes an elongate shaft 22 having a proximal end and a distal end and a head 24 at the proximal end thereof. As shown, elongate shaft 22 is a screw shaft having threads 26 therealong. Head 24 includes a pair of slots 28 that extend in a proximal-distal direction aligned with the longitudinal axis L-L.

The tulip 14 has a bore 32 therethrough that is dimensioned to allow the distal end of elongate shaft 12 to pass therethrough, but the dimension of the distal opening 32D is smaller than the largest cross-sectional dimension of the head 24, and thereby prevents passage of the head 24 therethrough, as illustrated in FIGS. 1A-1E. Inserts 18 are fixed at 34 to tulip 14 as shown in FIG. 1C, so as to protrude into the bore 32. Slots 28 are configured and dimensioned to receive the protruding ends of inserts 18, to allow inserts 18 to freely slide therein in the proximal distal direction, but to prevent movements in any other directions. Inserts 18 may be fixed to tulip 14 by adhesives, welding, press fitting and/or other fixation expedients, preferably by press fitting into receptacles 34 formed in tulip 14. As shown in FIGS. 1C-1E, slots 28 are formed diametrically opposite one another, separated by 180 degrees around the head 24. This is necessary to allow both inserts 18 to slide in the same plane, resulting in an assembly that allows the elongate shaft 22 to pivot relative to the tulip 14 in one plane only. FIG. 1C shows a longitudinal sectional view of assembly 10 taken along line 1C-1C of FIG. 1A. FIGS. 1A-1C illustrate the assembly 10 where the fastener 12 is aligned with the longitudinal axis L-L of the assembly 10 and tulip 14. FIG. 1D shows the longitudinal sectional view of FIG. 1C, but after uniplanar pivoting of fastener 12/shaft 22 relative to tulip 14 by an angle 36 (as shown by the angle 36 between the longitudinal axis L'-L' of the fastener 12 and the longitudinal axis L-L of the tulip 14. The uniplanar range of motion may include angulation of up to about ±40°, typically a range of up to about ±22°, wherein the plus and minus values indicate the angle 36 in the direction shown in FIG. 1D and the same amount of angulation in the opposite direction in that plane.

Saddle 16 is configured and dimensioned to be fixed relative to tulip 14 while abutting the proximal portion of head 24 as shown in FIG. 1C. Saddle 16 has a concave distal surface 16s configured and dimensioned as a bearing surface to allow the convex curvature of head 24 to slide relative thereto. Accordingly, as shaft 22 is pivoted relative to tulip 14, head 24 rotates against bearing surfaces of the tulip 14 and saddle 16, as illustrated in FIG. 1D. FIG. 1D illustrates a maximum angle 36 of pivoting, as inserts 18 make contact with the ends of slots 28, respectively. As shown in FIG. 1E, inserts 18 are centered in slots 28 when shaft 22 is aligned with the longitudinal axis L-L of the tulip 14. Alternatively, slots 28 could be asymmetrically formed so as to allow angulation 36 on one side of the longitudinal axis L-L to be greater than angulation on the other side (angulation the opposite direction).

In the embodiment shown, saddle 16 is a standard saddle and is configured and dimensioned to be retained by shoulder 14S when fitted into tulip 14, see FIG. 1G. The saddle-shaped tulip 14 further includes a slot 14ST passing therethrough, as shown in FIGS. 1A and 1G that is configured and dimensioned to receive an orthopedic rod or plate therein, in manners known in the art. Threading 14X allows a set screw 46 or the like to be torqued against the rod/plate 50 to fix it relative to the tulip 14 (see FIG. 10). The saddle 16 is configured to apply compression to the head 24 to lock an orientation of the fastener 12 relative to the tulip 14, thereby even preventing the movement in the one plane that is otherwise allowed, and thus preventing movement in all planes. The set screw 46 presses on the rod or plate 50 and the head 24 of the shaft is squeezed in between the saddle and the bottom of the tulip 14.

All components 12, 14, 16 and 18 of assembly 10 are preferably made of titanium. Alternatively, one or more components may be made of stainless steel, or other known, rigid materials used as substitute materials in the art, which may include other biocompatible metals, plastics and/or composites. The uniplanar angulation of assembly 10 may vary, but preferably has a range of about eighty degrees (twice angle 36). The dimensions of the components will vary depending upon the location of the spine in which they are used, the size of the patient (e.g., pediatric vs. adult, male vs. female, etc.), etc. The outside diameter of tulip 14 typically falls within a range of about 8 mm to about 15 mm. The outside diameter of shaft 22 typically falls within a range of about 3 mm to about 8.5 mm. The length of shaft 22 typically falls within a range of about 10 mm to about 100 mm. The height 18H of insert 18 is about 1 mm to about 2 mm, typically about 1.5 mm. The length 18L: of insert 18 is about 1.5 mm to about 3 mm, typically about 2.25 mm.

Referring now to FIG. 2A, a plan view of a uniplanar surgical screw assembly 10 is shown, according to another embodiment of the present invention. FIG. 2B shows assembly 10 having been rotated about its longitudinal axis L-L by ninety degrees, relative to the view shown in FIG. 2A. The assembly 10 of the embodiment of FIGS. 2A-2J includes a fastener 12 (see the isolated view of FIG. 2G), a saddle-shaped tulip 14 (see the isolated view of FIG. 2H), a saddle 16 (see the isolated view of FIG. 2I) and only one insert 18 (see isolated view in FIG. 2J), in contrast to the pair of inserts 18 employed in the embodiment of FIGS. 1A-1J.

Fastener 12 includes an elongate shaft 22 having a proximal end and a distal end and a head 24 at the proximal end thereof. As shown, elongate shaft 22 is a screw shaft having threads 26 therealong. Head 24 includes a slot 28 that extends in a proximal-distal direction aligned with the longitudinal axis L-L.

The tulip 14 has a bore 32 therethrough that is dimensioned to allow the distal end of elongate shaft 12 to pass therethrough, but the dimension of the distal opening 32D is smaller than the largest cross-sectional dimension of the head 24, and thereby prevents passage of the head 24 therethrough, as illustrated in FIGS. 2A-2E. Insert 18 is fixed at 34 to tulip 14 as shown in FIG. 2E, so as to protrude into the bore 32. Slot 28 is configured and dimensioned to receive the protruding end of insert 18, to allow insert 18 to freely slide therein in the proximal distal direction, but to prevent movements in any other directions. Insert 18 may be fixed to tulip 14 by adhesives, welding, press fitting and/or other fixation expedients, preferably by press fitting into receptacle 34 formed in tulip 14. Slot 28 is formed to allow insert 18 to slide only in a proximal-distal direction that permits pivoting of the shaft 22 relative to the tulip 14 in one plane only. FIG. 2C shows a longitudinal sectional view of assembly 10 taken along line 2C-2C of FIG. 2A. FIGS. 2A-2C illustrate the assembly 10 where the fastener 12 is aligned with the longitudinal axis L-L of the assembly 10 and tulip 14. FIG. 2D shows the longitudinal sectional view of FIG. 2C, but after uniplanar pivoting of fastener 12/shaft 22 relative to tulip 14 by an angle 36 (as shown by the angle 36 between the longitudinal axis L'-L' of the fastener 12 and the longitudinal axis L-L of the tulip 14.

Saddle 16 is configured and dimensioned to be fixed relative to tulip 14 while abutting the proximal portion of head 24 as shown in FIG. 2C. Saddle 16 has a concave distal surface 16S configured and dimensioned as a bearing surface to allow the convex curvature of head 24 to slide relative thereto. Accordingly, as shaft 22 is pivoted relative to tulip 14, head 24 rotates against bearing surfaces of the tulip 14 and saddle 16, as illustrated in FIG. 2D. FIG. 2D illustrates a maximum angle 36 of pivoting in one direction, as insert 18 makes contact with the end of slot 28. As shown in FIG. 2E, insert 18 is centered in slot 28 when shaft 22 is aligned with the longitudinal axis L-L of the tulip 14. Alternatively, slot 28 could be asymmetrically formed so as to allow angulation 36 on one side of the longitudinal axis L-L to be greater than angulation on the other side (angulation the opposite direction).

In the embodiment shown, saddle 16 is a standard saddle and is configured and dimensioned to be retained by shoulder 14S when fitted into tulip 14, see FIG. 2H. The saddle-shaped tulip 14 further includes a slot 14ST passing therethrough, as shown in FIGS. 2A and 2G that is configured and dimensioned to receive an orthopedic rod or plate therein, in manners known in the art. Threading 14X allows a set screw (not shown) or the like to be torqued against the rod/plate to fix it relative to the tulip 14. The saddle 16 is configured to apply compression to the head 24 to lock an orientation of the fastener 12 relative to the tulip 14, thereby even preventing the movement in the one plane that is otherwise allowed, and thus preventing movement in all planes, by locking down with the set screw in a manner described above.

All components 12, 14, 16 and 18 of assembly 10 are preferably made of titanium. Alternatively, one or more components may be made of alternative materials, the same as described above with regard to the previous embodiment. The uniplanar angulation of assembly 10 may vary, but preferably has a range of about eighty (80) degrees (twice angle 36). The dimensions of the components will vary depending upon the location of the spine in which they are used, the size of the patient (e.g., pediatric vs. adult, male vs. female, etc.), etc. The outside diameter of tulip 14 typically falls within a range of about 8 mm to about 15 mm. The outside diameter of shaft 22 typically falls within a range of about 3 mm to about 8.5 mm. The length of shaft 22 typically falls within a range of about 10 mm to about 100 mm. The height 18H of insert 18 is about 1 mm to about 2 mm, typically about 1.5 mm. The length 18L of insert 18 is about 1.5 mm to about 3 mm, typically about 2.25 mm.

FIG. 3A is a plan view of a uniplanar surgical screw assembly 10 according to another embodiment of the present invention. FIG. 3B shows assembly 10 having been rotated about its longitudinal axis L-L by ninety degrees, relative to the view shown in FIG. 3A. The assembly 10 of the embodiment of FIGS. 3A-3I includes a fastener 12 (see the isolated view of FIG. 3G), a saddle-shaped tulip 14 (see the isolated view of FIG. 3H), and a saddle 16 (see the isolated view of FIG. 3I). Rather than employing one or more inserts 18, the embodiment of FIGS. 3A-3I provides protrusions 48 integrally formed with tulip 14 and protruding into the open space formed by the bore 32, as shown in FIGS. 3C-3F.

Fastener 12 includes an elongate shaft 22 having a proximal end and a distal end and a head 24 at the proximal end thereof. As shown, elongate shaft 22 is a screw shaft having threads 26 therealong. Head 24 includes a pair of slots 28 that extend in a proximal-distal direction aligned with the longitudinal axis L-L.

The tulip 14 has a bore 32 therethrough that is dimensioned to allow the distal end of elongate shaft 22 to pass therethrough, but the dimension of the distal opening 32D is smaller than the largest cross-sectional dimension of the head 24, and thereby prevents passage of the head 24 therethrough, as illustrated in FIGS. 3A-3E. Slots 28 are configured and dimensioned to receive the protruding ends of protrusions 48, to allow protrusions 48 to freely slide therein in the proximal distal direction, but to prevent movements in any other directions. As shown in FIGS. 3C-3F, slots 28 are formed diametrically opposite one another, separated by 180 degrees around the head 24. This is necessary to allow both protrusions 48 to slide in the same plane, resulting in an assembly that allows the elongate shaft 22 to pivot relative to the tulip 14 in one plane only. FIG. 3C shows a longitudinal sectional view of assembly 10 taken along line 3C-3C of FIG. 1A. FIGS. 3A-3C illustrate the assembly 10 where the fastener 12 is aligned with the longitudinal axis L-L of the assembly 10 and tulip 14. FIG. 3D shows the longitudinal sectional view of FIG. 3C, but after uniplanar pivoting of fastener 12/shaft 22 relative to tulip 14 by an angle 36 (as shown by the angle 36 between the longitudinal axis L'-L' of the fastener 12 and the longitudinal axis L-L of the tulip 14.

Saddle 16 is configured and dimensioned to be fixed relative to tulip 14 while abutting the proximal portion of head 24 as shown in FIG. 3C. Saddle 16 has a concave distal surface 16S configured and dimensioned as a bearing surface to allow the convex curvature of head 24 to slide relative thereto. Accordingly, as shaft 22 is pivoted relative to tulip 14, head 24 rotates against bearing surfaces of the tulip 14 and saddle 16, as illustrated in FIG. 3D. FIG. 3D illustrates a maximum angle 36 of pivoting, as protrusions 48 make contact with the ends of slots 28, respectively. As shown in FIG. 3E (enlarged view of the portion of FIG. 3C identified within circle 3E), protrusions 48 are centered in slots 28 when shaft 22 is aligned with the longitudinal axis L-L of the tulip 14. Alternatively, slots 28 could be asymmetrically formed so as to allow angulation 36 on one side of the longitudinal axis L-L to be greater than angulation on the other side (angulation in the opposite direction).

In the embodiment shown, saddle 16 is a standard saddle and is configured and dimensioned to be retained by shoulder 14S when fitted into tulip 14, see FIG. 3H. The saddle-shaped tulip 14 further includes a slot 14ST passing therethrough, as shown in FIGS. 3A and 3H that is configured and dimensioned to receive an orthopedic rod or plate therein, in manners known in the art. Threading 14X allows a set screw (not shown) or the like to be torqued against the rod/plate to fix it relative to the tulip 14. The saddle 16 is configured to apply compression to the head 24 to lock an orientation of the fastener 12 relative to the tulip 14, thereby even preventing the movement in the one plane that is otherwise allowed, and thus preventing movement in all planes, such as in a manner already previously described.

All components 12, 14, 16 and 48 of assembly 10 are preferably made of titanium. Alternatively, one or more components may be made of one or more alternative materials such as described in regard to previous embodiments. The uniplanar angulation of assembly 10 may vary, but preferably has a range of about eighty (80) degrees (twice angle 36). The dimensions of the components will vary depending upon the location of the spine in which they are used, the size of the patient (e.g., pediatric vs. adult, male vs. female, etc.), etc. The outside diameter of tulip 14 typically falls within a range of about 8 mm to about 15 mm. The outside diameter of shaft 22 typically falls within a range of about 3 mm to about 8.5 mm. The length of shaft 22 typically falls within a range of about 10 mm to about 100 mm. The height 48H of protrusion 48 is about 1 mm to about 2 mm, typically about 1.5 mm. The length 48L: of protrusion 48 is about 1.5 mm to about 3 mm, typically about 2.25 mm.

Figure 4G:
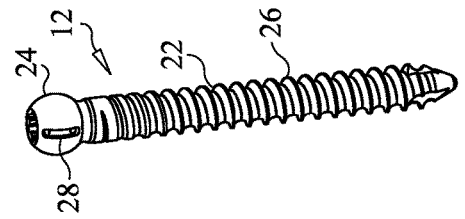
FIG. 4G is an isolated, perspective view of the fastener of FIG. 4A.
Figure 4D:
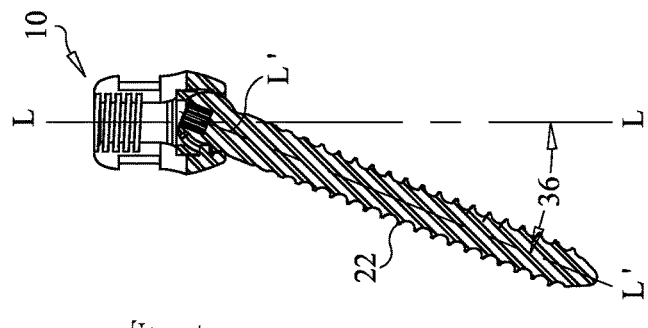
FIG. 4D shows the assembly of FIG. 4C, after pivoting the shaft relative to the tulip.
Figure 4C:
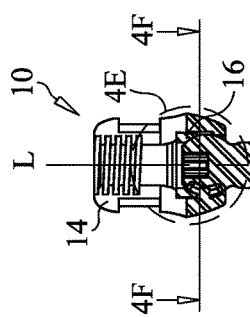
FIG. 4C is a longitudinal sectional view of the embodiment of FIG. 4A taken along line 4C-4C.
Figure 4B:
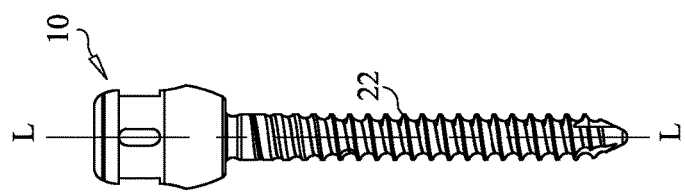
FIG. 4B shows the assembly of FIG. 4A having been rotated about its longitudinal axis L-L by ninety degrees, relative to the view shown in FIG. 4A.
Figure 4A:
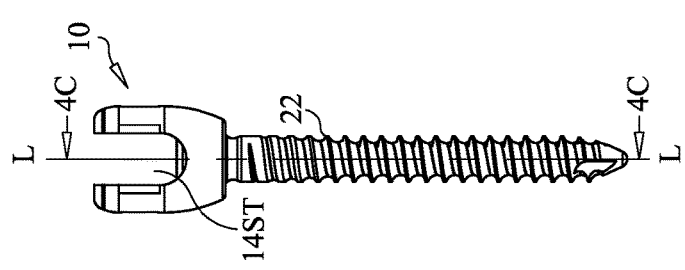
FIG. 4A is a plan view of a uniplanar surgical screw assembly according to another embodiment of the present invention.
Figure 4I:
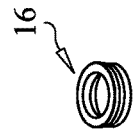
FIG. 4I is an isolated, perspective view of the saddle component of FIG. 4A.

FIG. 4A is a plan view of a uniplanar surgical screw assembly 10 according to another embodiment of the present invention. FIG. 4B shows assembly 10 having been rotated about its longitudinal axis L-L by ninety degrees, relative to the view shown in FIG. 4A. The assembly 10 of the embodiment of FIGS. 4A-2I includes a fastener 12 (see the isolated view of FIG. 4G), a saddle-shaped tulip 14 (see the isolated view of FIG. 4H), a saddle 16 (see the isolated view of FIG. 4I) and only one protrusion 48 (see FIGS. 4C-4F), in contrast to the pair of protrusions 48 employed in the embodiment of FIGS. 3A-3I.

Fastener 12 includes an elongate shaft 22 having a proximal end and a distal end and a head 24 at the proximal end thereof. As shown, elongate shaft 22 is a screw shaft having threads 26 therealong. Head 24 includes a slot 28 that extends in a proximal-distal direction aligned with the longitudinal axis L-L.

The tulip 14 has a bore 32 therethrough that is dimensioned to allow the distal end of elongate shaft 12 to pass therethrough, but the cross-sectional dimension of the distal opening 32D is smaller than the largest cross-sectional dimension of the head 24, and thereby prevents passage of the head 24 therethrough, as illustrated in FIGS. 4A-4E. Protrusion 48 is integral with tulip 14 and protrudes into the bore 32, as illustrated in FIGS. 4C-4F. Slot 28 is configured and dimensioned to receive the protruding end of protrusion 48, to allow protrusion 48 to freely slide therein in the proximal distal direction, but to prevent movements in any other directions. Slot 28 is formed to allow protrusion 48 to slide only in a proximal-distal direction that permits pivoting of the shaft 22 relative to the tulip 14 in one plane only. FIG. 4C shows a longitudinal sectional view of assembly 10 taken along line 4C-4C of FIG. 4A. FIGS. 4A-4C illustrate the assembly 10 where the fastener 12 is aligned with the longitudinal axis L-L of the assembly 10 and tulip 14. FIG. 4D shows the longitudinal sectional view of FIG. 4C, but after uniplanar pivoting of fastener 12/shaft 22 relative to tulip 14 by an angle 36 (as shown by the angle 36 between the longitudinal axis L'-L' of the fastener 12 and the longitudinal axis L-L of the tulip 14.

Saddle 16 is configured and dimensioned to be fixed relative to tulip 14 while abutting the proximal portion of head 24 as shown in FIG. 4C. Saddle 16 has a concave distal surface 16S configured and dimensioned as a bearing surface to allow the convex curvature of head 24 to slide relative thereto. Accordingly, as shaft 22 is pivots relative to tulip 14, head 24 rotates against bearing surfaces of the tulip 14 and saddle 16, as illustrated in FIG. 4D. FIG. 4D illustrates a maximum angle 36 of pivoting in one direction, as protrusion 48 makes contact with the end of slot 28. As shown in FIG. 4E, protrusion 48 is centered in slot 28 when shaft 22 is aligned with the longitudinal axis L-L of the tulip 14. Alternatively, slot 28 could be asymmetrically formed so as to allow angulation 36 on one side of the longitudinal axis L-L to be greater than angulation on the other side (angulation in the opposite direction).

Figure 4H:
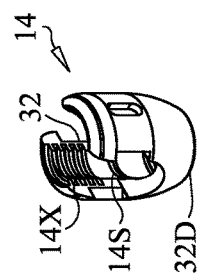
FIG. 4H is an isolated, perspective view of the tulip component of FIG. 4A.
Figure 4F:
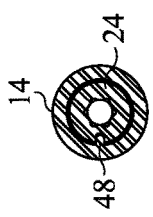
FIG. 4F is a cross sectional view of the assembly taken along line 4F-4F in FIG. 4C.

In the embodiment shown, saddle 16 is a standard saddle and is configured and dimensioned to be retained by shoulder 14S when fitted into tulip 14, see FIG. 4H. The saddle-shaped tulip 14 further includes a slot 14ST passing therethrough, as shown in FIGS. 2A and 2G that is configured and dimensioned to receive an orthopedic rod or plate therein, in manners known in the art. Threading 14X allows a set screw (not shown) or the like to be torqued against the rod/plate to fix it relative to the tulip 14. The saddle 16 is configured to apply compression to the head 24 to lock an orientation of the fastener 12 relative to the tulip 14, thereby even preventing the movement in the one plane that is otherwise allowed, and thus preventing movement in all planes, such as in a manner described in previous embodiments.

All components 12, 14, 16 and 18 of assembly 10 are preferably made of titanium. One or more components may be made of an alternative material, like described in previous embodiments. The uniplanar angulation of assembly 10 may vary, but preferably has a range of about eighty (80) degrees (twice angle 36). The dimensions of the components will vary depending upon the location of the spine in which they are used, the size of the patient (e.g., pediatric vs. adult, male vs. female, etc.), etc. The outside diameter of tulip 14 typically falls within a range of about 8 mm to about 15 mm. The outside diameter of shaft 22 typically falls within a range of about 3 mm to about 8.5 mm. The length of shaft 22 typically falls within a range of about 10 mm to about 100 mm. The height 18H of insert 18 is about 1 mm to about 2 mm, typically about 1.5 mm. The length 18L of insert 18 is about 1.5 mm to about 3 mm, typically about 2.25 mm.

FIG. 5A is a plan view of a uniplanar surgical screw assembly 10, according to another embodiment of the present invention. FIG. 5E shows assembly 10 having been rotated about its longitudinal axis L-L by ninety degrees, relative to the view shown in FIG. 5A. The assembly 10 of the embodiment of FIGS. 5A-5J includes a fastener 12 (see the isolated view of FIG. 5G), a saddle-shaped tulip 14 (see the isolated view of FIG. 5H), a saddle 16 (see the isolated view of FIG. 5I) and a pair of flat inserts 58 (see isolated view of a flat insert 58 in FIG. 5J).

Fastener 12 includes an elongate shaft 22 having a proximal end and a distal end and a head 24 at the proximal end thereof. As shown, elongate shaft 22 is a screw shaft having threads 26 therealong. Head 24 includes a pair of flats 68 on an otherwise convex surface, typically an otherwise spherical surface. The surfaces of flats 68 are substantially parallel to one another as shown in FIGS. 5C-5D.

The tulip 14 has a bore 32 therethrough that is dimensioned to allow the distal end of elongate shaft 12 to pass therethrough, but the cross-sectional dimension of the distal opening 32D is smaller than the largest cross-sectional dimension of the head 24, and thereby prevents passage of the head 24 therethrough, as illustrated in FIGS. 5A-5B and 5D-5F. Flat inserts 58 are received in receptacles 64 formed in tulip 14 as shown in FIGS. 5C-5D, in an orientation, so that the flat surface 58F of flat insert 58 interfaces with flat 68 of head 24, as also shown in FIGS. 5C-5D. The interaction between the flats 68 and flat sides 58F prevents all pivoting of the shaft 22 relative to the tulip 14, except for in one plane, that plane being parallel to the flats 68 and flat sides 58F. The non-flat side of insert 58 is received in receptacle 64 which has a shape that mates with the non-flat side of the insert 58.

The non-flat side of insert 58 is shaped and configured to prevent the flat insert 58 from sliding relative to the receptacle 64. In the embodiment shown in FIG. 5J, the non-flat side comprises a proximal end portion 58P, a central portion 58C, and a distal end portion 58D, wherein the central portion 58C extends further from the flat side 58D than the distances by which the proximal 58P and distal 58D end portions extend from the flat side 58F. In the embodiment shown in FIG. 5J, the central portion has a first curvature and the proximal and distal end portions have a second curvature, the first curvature having a smaller radius of curvature than the second curvature. In the embodiment of FIG. 5J, the non-flat side includes a bulbous portion 58C extending further from the flat side than an extent to which a remainder (58Pm 58D) of the non-flat side extends from the flat side 58F.

Flat inserts 58 may be fixed to tulip 14 by adhesives, welding, press fitting and/or other fixation expedients, or loosely fit within tulip 14. As shown in FIGS. 5C-5D, flats 68 are formed diametrically opposite one another on head 24, so as to be parallel to one another. This is necessary to allow the flats 68 to rotate relative to the flat inserts 58 as shaft 22 is pivoted relative to tulip 14, such as is shown in FIG. 5F. Thus, flats 68 and flat surface 58F are all oriented in substantially parallel planes to maintain uniplanar movement of the shaft 22 relative to the tulip 14.

FIG. 5B shows a longitudinal sectional view of assembly 10 taken along line 5B-5B of FIG. 5E. FIGS. 5A-5C illustrate the assembly 10 where the fastener 12 is aligned with the longitudinal axis L-L of the assembly 10 and tulip 14. FIG. 5F shows the longitudinal sectional view of FIG. 5B, but after uniplanar pivoting of fastener 12/shaft 22 relative to tulip 14 by an angle 36 (as shown by the angle 36 between the longitudinal axis L'-L' of the fastener 12 and the longitudinal axis L-L of the tulip 14.

Saddle 16 is configured and dimensioned to be fixed relative to tulip 14 while abutting the proximal portion of head 24 as shown in FIG. 5D. Saddle 16 has a concave distal surface 16s configured and dimensioned as a bearing surface to allow the convex curvature of head 24 to slide relative thereto. Accordingly, as shaft 22 is pivoted relative to tulip 14, head 24 rotates against bearing surfaces of the tulip 14 and saddle 16, as illustrated in FIG. 5F. FIG. 5F illustrates a maximum angle 36 of pivoting. The limits of pivoting are established by the shaft 22 contacting against the tulip 14.

In the embodiment shown, saddle 16 is a standard saddle and is configured and dimensioned to be retained by shoulder 14S when fitted into tulip 14, see FIG. 5h. The saddle-shaped tulip 14 further includes a slot 14ST passing therethrough, as shown in FIGS. 5B and 5H that is configured and dimensioned to receive an orthopedic rod or plate therein, in manners known in the art. Threading 14X allows a set screw (not shown) or the like to be torqued against the rod/plate to fix it relative to the tulip 14.

All components 12, 14, 16 and 58 of assembly 10 are preferably made of titanium. One or more components may be made of an alternative material such as described above. The uniplanar angulation of assembly 10 may vary, but preferably has a range of about 80 degrees (twice angle 36). The dimensions of the components will vary depending upon the location of the spine in which they are used, the size of the patient (e.g., pediatric vs. adult, male vs. female, etc.), etc. The outside diameter of tulip 14 typically falls within a range of about 8 mm to about 15 mm. The outside diameter of shaft 22 typically falls within a range of about 3 mm to about 8.5 mm. The length of shaft 22 typically falls within a range of about 10 mm to about 100 mm. The length 58L of insert 58 is about 4.5 mm to about 6.5 mm, typically about 5.3 mm.

FIG. 6A is a plan view of a uniplanar surgical screw assembly 10, according to another embodiment of the present invention. FIG. 6E shows assembly 10 having been rotated about its longitudinal axis L-L by ninety degrees, relative to the view shown in FIG. 6A. The assembly 10 of the embodiment of FIGS. 6A-6J includes a fastener 12 (see the isolated view of FIG. 6G), a saddle-shaped tulip 14 (see the isolated view of FIG. 6H), a saddle 16 (see the isolated view of FIG. 6I) and a single flat insert 58 (see isolated view of FIG. 5J).

Fastener 12 includes an elongate shaft 22 having a proximal end and a distal end and a head 24 at the proximal end thereof. As shown, elongate shaft 22 is a screw shaft having threads 26 therealong. Head 24 includes a flat 68 on an otherwise convex surface, typically an otherwise spherical surface. The surface of flat 68 is substantially parallel to the longitudinal axis L'-L' of the fastener 12, as shown in FIG. 6G.

The tulip 14 has a bore 32 therethrough that is dimensioned to allow the distal end of elongate shaft 22 to pass therethrough, but the cross-sectional dimension of the distal opening 32D is smaller than the largest cross-sectional dimension of the head 24, and thereby prevents passage of the head 24 therethrough, as illustrated in FIGS. 6A-6B and 6D-6F. Flat insert 58 is received in receptacle 64 formed in tulip 14 as shown in FIGS. 6C-6D, in an orientation, so that the flat surface 58F of flat insert 58 interfaces with flat 68 of head 24, as also shown in FIGS. 6C-6D. The interaction between the flat 68 and flat side 58F prevents all pivoting of the shaft 22 relative to the tulip 14, except for in one plane, that plane being parallel to the flat 68 and flat side 58F. The non-flat side of insert 58 is received in receptacle 64 which has a shape that mates with the non-flat side of the insert 58.

The non-flat side of insert 58 is shaped and configured to prevent the flat insert 58 from sliding relative to the receptacle 64. In the embodiment shown in FIG. 6J, the non-flat side comprises a proximal end portion 58P, a central portion 58C, and a distal end portion 58D, wherein the central portion 58C extends further from the flat side 58D than the distances by which the proximal 58P and distal 58D end portions extend from the flat side 58F. In the embodiment shown in FIG. 6J, the central portion has a first curvature and the proximal and distal end portions have a second curvature, the first curvature having a smaller radius of curvature than the second curvature. In the embodiment of FIG. 5J, the non-flat side includes a bulbous portion 58C extending further from the flat side than an extent to which a remainder (58Pm 58D) of the non-flat side extends from the flat side 58F.

Flat insert 58 may be fixed to tulip 14 by adhesives, welding, press fitting and/or other fixation expedients, or may be loosely fitted in tulip 14. As shown in FIGS. 6C-6D, the surface of flat 68 is parallel to the flat surface 58F. This is necessary to allow the flat 68 to rotate relative to the flat insert 58 as shaft 22 is pivoted relative to tulip 14, such as is shown in FIG. 6F. Thus, flat 68 and flat surface 58F are oriented in substantially parallel planes to maintain uniplanar movement of the shaft 22 relative to the tulip 14.

FIG. 6B shows a longitudinal sectional view of assembly 10 taken along line 6B-6B of FIG. 6E. FIGS. 6A-6C illustrate the assembly 10 where the fastener 12 is aligned with the longitudinal axis L-L of the assembly 10 and tulip 14. FIG. 6F shows the longitudinal sectional view of FIG. 6B, but after uniplanar pivoting of fastener 12/shaft 22 relative to tulip 14 by an angle 36 (as shown by the angle 36 between the longitudinal axis L'-L' of the fastener 12 and the longitudinal axis L-L of the tulip 14.

Saddle 16 is configured and dimensioned to be fixed relative to tulip 14 while abutting the proximal portion of head 24 as shown in FIG. 6D. Saddle 16 has a concave distal surface 16s configured and dimensioned as a bearing surface to allow the convex curvature of head 24 to slide relative thereto. Accordingly, as shaft 22 is pivoted relative to tulip 14, head 24 rotates against bearing surfaces of the tulip 14 and saddle 16, as illustrated in FIG. 6F. FIG. 6F illustrates a maximum angle 36 of pivoting, as limited by the shaft contacting the tulip.

In the embodiment shown, saddle 16 is a standard saddle and is configured and dimensioned to be retained by shoulder 14S when fitted into tulip 14, see FIGS. 6F and 6H. The saddle-shaped tulip 14 further includes a slot 14ST passing therethrough, as shown in FIGS. 6E and 6H that is configured and dimensioned to receive an orthopedic rod or plate therein, in manners known in the art. Threading 14X allows a set screw (not shown) or the like to be torqued against the rod/plate to fix it relative to the tulip 14.

All components 12, 14, 16 and 58 of assembly 10 are preferably made of titanium. One or more components may be made of an alternative material, such as described above with regard to previous embodiments. The uniplanar angulation of assembly 10 may vary, but preferably has a range of about 80 degrees (twice angle 36). The dimensions of the components will vary depending upon the location of the spine in which they are used, the size of the patient (e.g., pediatric vs. adult, male vs. female, etc.), etc. The outside diameter of tulip 14 typically falls within a range of about 8 mm to about 15 mm. The outside diameter of shaft 22 typically falls within a range of about 3 mm to about 8.5 mm. The length of shaft 22 typically falls within a range of about 10 mm to about 100 mm. The length 58L of insert 58 is about 4.5 mm to about 6.5 mm, typically about 5.3 mm.

FIG. 7A is a plan view of a uniplanar surgical screw assembly 10, according to another embodiment of the present invention. FIG. 7B shows assembly 10 having been rotated about its longitudinal axis L-L by ninety degrees, relative to the view shown in FIG. 7A. The assembly 10 of the embodiment of FIGS. 7A-7I includes a fastener 12 (see the isolated view of FIG. 7G), a saddle-shaped tulip 14 (see the isolated view of FIG. 7H), and a saddle 16 (see the isolated view of FIG. 7I).

Fastener 12 includes an elongate shaft 22 having a proximal end and a distal end and a head 24 at the proximal end thereof. As shown, elongate shaft 22 is a screw shaft having threads 26 therealong. Head 24 includes a pair of protrusions 78 extending from diametrically opposite sides of a convex surface. Protrusions 78 may be inserts fixed to head 24, but are preferably integrally formed therewith.

The tulip 14 has a bore 32 therethrough that is dimensioned to allow the distal end of elongate shaft 12 to pass therethrough, but the cross-sectional dimension of the distal opening 32D is smaller than the largest cross-sectional dimension of the head 24, and thereby prevents passage of the head 24 therethrough, as illustrated in FIGS. 7A-7E. Slots 88 are formed in the inner surface of tulip 14 as shown in FIG. 7E. Slots 88 each extend in a proximal-distal direction and are formed diametrically opposite one another. Slots 88 are configured and dimensioned to receive the protruding ends of protrusions 78, to allow protrusions 78 to freely slide therein in the proximal-distal directions, but to prevent movements in any other directions, i.e., only uniplanar pivoting is allowed. AS noted, protrusions 78 are preferably integral with head 24, but when fixed thereto, may be fixed to head 24 by adhesives, welding, press fitting and/or other fixation expedients, preferably by press fitting into receptacles formed in the head 24. As shown in FIGS. 7C-7F, slots 88 are formed diametrically opposite one another, separated by 180 degrees around the tulip 14. This is necessary to allow both protrusions 78 to slide in the same plane, resulting in an assembly that allows the elongate shaft 22 to pivot relative to the tulip 14 in one plane only. FIG. 7C shows a longitudinal sectional view of assembly 10 taken along line 7C-7C of FIG. 7A. FIGS. 7A-7C illustrate the assembly 10 where the fastener 12 is aligned with the longitudinal axis L-L of the assembly 10 and tulip 14. FIG. 7D shows the longitudinal sectional view of FIG. 7C, but after uniplanar pivoting of fastener 12/shaft 22 relative to tulip 14 by an angle 36 (as shown by the angle 36 between the longitudinal axis L'-L' of the fastener 12 and the longitudinal axis L-L of the tulip 14.

Saddle 16 is configured and dimensioned to be fixed relative to tulip 14 while abutting the proximal portion of head 24 as shown in FIG. 1C. Saddle 16 has a concave distal surface 16S configured and dimensioned as a bearing surface to allow the convex curvature of head 24 to slide relative thereto. Additionally, in this embodiment, saddle 16 includes a pair of diametrically opposed notches in the bottom surface thereof that are configured and dimensioned to slidably fit over the protrusions 78.

As shaft 22 is pivoted relative to tulip 14, head 24 rotates against bearing surfaces of the tulip 14 and saddle 16, as illustrated in FIG. 7D. FIG. 7D illustrates a maximum angle 36 of pivoting, as protrusions 78 make contact with the ends of slots 88, respectively. As shown in FIG. 7E, protrusions 78 are centered in slots 88 when shaft 22 is aligned with the longitudinal axis L-L of the tulip 14.

Alternatively, slots 88 could be asymmetrically formed so as to allow angulation 36 on one side of the longitudinal axis L-L to be greater than angulation on the other side (angulation in the opposite direction).

In the embodiment shown, saddle 16 is configured and dimensioned to be retained by shoulder 14S when fitted into tulip 14, see FIGS. 7E and 7H. The saddle-shaped tulip 14 further includes a slot 14ST passing therethrough, as shown in FIGS. 7A and 7H that is configured and dimensioned to receive an orthopedic rod or plate therein, in manners known in the art. Threading 14X allows a set screw (not shown) or the like to be torqued against the rod/plate to fix it relative to the tulip 14. The saddle 16 is configured to apply compression to the head 24 to lock an orientation of the fastener 12 relative to the tulip 14, thereby even preventing the movement in the one plane that is otherwise allowed, and thus preventing movement in all planes.

All components 12, 14, 16 and 78 of assembly 10 are preferably made of titanium. One or more components may be made of an alternative material, like previous embodiments described above. The uniplanar angulation of assembly 10 may vary, but preferably has a range of about 80 degrees (twice angle 36). The dimensions of the components will vary depending upon the location of the spine in which they are used, the size of the patient (e.g., pediatric vs. adult, male vs. female, etc.), etc. The outside diameter of tulip 14 typically falls within a range of about 8 mm to about 15 mm. The outside diameter of shaft 22 typically falls within a range of about 3 mm to about 8.5 mm. The length of shaft 22 typically falls within a range of about 10 mm to about 100 mm. The height 78H of protrusion 78 is in the range from about 1 mm to about 3 mm, typically about 2 mm. The width 78W of protrusion 78 is within a range of from about 1 mm to about 2.5 mm, typically about 1.75 mm.

FIG. 8A is a plan view of a uniplanar surgical screw assembly 10, according to another embodiment of the present invention. FIG. 8B shows assembly 10 having been rotated about its longitudinal axis L-L by ninety degrees, relative to the view shown in FIG. 8A. The assembly 10 of the embodiment of FIGS. 8A-8I includes a fastener 12 (see the isolated view of FIG. 8G), a saddle-shaped tulip 14 (see the isolated view of FIG. 8H), and a saddle 16 (see the isolated view of FIG. 8I).

Fastener 12 includes an elongate shaft 22 having a proximal end and a distal end and a head 24 at the proximal end thereof. As shown, elongate shaft 22 is a screw shaft having threads 26 therealong. Head 24 includes a single protrusion 78 extending from a side of a convex surface thereof. Protrusion 78 may be an insert fixed to head 24, but is preferably integrally formed therewith.

The tulip 14 has a bore 32 therethrough that is dimensioned to allow the distal end of elongate shaft 22 to pass therethrough, but the cross-sectional dimension of the distal opening 32D is smaller than the largest cross-sectional dimension of the head 24, and thereby prevents passage of the head 24 therethrough, as illustrated in FIGS. 8A-8E. A slot 88 is formed in the inner surface on one side of the tulip 14 as shown in FIG. 8E. Slot 88 extends in a proximal-distal direction and is formed in a direction parallel to the longitudinal axis L-L. Slot 88 is configured and dimensioned to receive the protruding end of protrusion 78, to allow protrusion 78 to freely slide therein in the proximal-distal directions, but to prevent movements in any other directions, i.e., only uniplanar pivoting is allowed. As noted, protrusion 78 is preferably integral with head 24, but when fixed thereto, may be fixed to head 24 by adhesives, welding, press fitting and/or other fixation expedients, preferably by press fitting into receptacles formed in the head 24. As shown in FIGS. 8C-8F, slot 88 is formed to receive protrusion 78 therein, to allow protrusion 78 to slide in a plane, resulting in an assembly that allows the elongate shaft 22 to pivot relative to the tulip 14 in one plane only. FIG. 8C shows a longitudinal sectional view of assembly 10 taken along line 8C-8C of FIG. 8A. FIGS. 8A-8C illustrate the assembly 10 where the fastener 12 is aligned with the longitudinal axis L-L of the assembly 10 and tulip 14. FIG. 8D shows the longitudinal sectional view of FIG. 8C, but after uniplanar pivoting of fastener 12/shaft 22 relative to tulip 14 by an angle 36 (as shown by the angle 36 between the longitudinal axis L'-L' of the fastener 12 and the longitudinal axis L-L of the tulip 14.

Saddle 16 is configured and dimensioned to be fixed relative to tulip 14 while abutting the proximal portion of head 24 as shown in FIG. 8C. Saddle 16 has a concave distal surface 16S configured and dimensioned as a bearing surface to allow the convex curvature of head 24 to slide relative thereto. Additionally, in this embodiment, saddle 16 includes a notch 90 in the bottom surface thereof that is configured and dimensioned to slidably fit over the protrusion 78.

As shaft 22 is pivoted relative to tulip 14, head 24 rotates against bearing surfaces of the tulip 14 and saddle 16, as illustrated in FIG. 8D. FIG. 8D illustrates a maximum angle 36 of pivoting, as protrusion 78 makes contact with the end of slot 88. As shown in FIG. 8E, protrusion 78 is centered in slot 88 when shaft 22 is aligned with the longitudinal axis L-L of the tulip 14. Alternatively, slot 88 could be asymmetrically formed so as to allow angulation 36 on one side of the longitudinal axis L-L to be greater than angulation on the other side (angulation in the opposite direction).

In the embodiment shown, saddle 16 is configured and dimensioned to be retained by shoulder 14S when fitted into tulip 14, see FIGS. 8E and 8H. The saddle-shaped tulip 14 further includes a slot 14ST passing therethrough, as shown in FIGS. 8A and 8H that is configured and dimensioned to receive an orthopedic rod or plate therein, in manners known in the art. Threading 14X allows a set screw (not shown) or the like to be torqued against the rod/plate to fix it relative to the tulip 14. The saddle 16 is configured to apply compression to the head 24 to lock an orientation of the fastener 12 relative to the tulip 14, thereby even preventing the movement in the one plane that is otherwise allowed, and thus preventing movement in all planes.

All components 12, 14, 16 and 78 of assembly 10 are preferably made of titanium. One or more components may be made of an alternative material such as described above with regard to previous embodiments. The uniplanar angulation of assembly 10 may vary, but preferably has a range of about 80 degrees (twice angle 36). The dimensions of the components will vary depending upon the location of the spine in which they are used, the size of the patient (e.g., pediatric vs. adult, male vs. female, etc.), etc. The outside diameter of tulip 14 typically falls within a range of about 8 mm to about 15 mm. The outside diameter of shaft 22 typically falls within a range of about 3 mm to about 8.5 mm. The length of shaft 22 typically falls within a range of about 10 mm to about 100 mm. The height 78H of protrusion 78 is in the range from about 1 mm to about 3 mm, typically about 2 mm. The width 78W of protrusion 78 is within a range of from about 1 mm to about 2.5 mm, typically about 1.75 mm.

FIG. 9A is a plan view of a uniplanar surgical screw assembly 10 according to another embodiment of the present invention. FIG. 9B shows assembly 10 having been rotated about its longitudinal axis L-L by ninety degrees, relative to the view shown in FIG. 9A. The assembly 10 of the embodiment of FIGS. 9A-9I includes a fastener 12 (see the isolated view of FIG. 9G), a saddle-shaped tulip 14 (see the isolated view of FIG. 9H), and a saddle 16 (see the isolated view of FIG. 9I). Rather than employing one or more inserts 18, the embodiment of FIGS. 3A-3I provides protrusions 98 integrally formed with saddle 16 and protruding inwardly, see FIGS. 9E, 9F and 9I.

Fastener 12 includes an elongate shaft 22 having a proximal end and a distal end and a head 24 at the proximal end thereof. As shown, elongate shaft 22 is a screw shaft having threads 26 therealong. Head 24 includes a pair of slots 108 that extend in a proximal-distal direction aligned with the longitudinal axis L-L.

The tulip 14 has a bore 32 therethrough that is dimensioned to allow the distal end of elongate shaft 22 to pass therethrough, but the cross-sectional dimension of the distal opening 32D is smaller than the largest cross-sectional dimension of the head 24, and thereby prevents passage of the head 24 therethrough, as illustrated in FIGS. 9A-9E. Slots 28 are configured and dimensioned to receive the protruding ends of protrusions 98, to allow protrusions 98 to freely slide therein in the proximal-distal direction, but to prevent movements in any other directions. As shown in FIGS. 9C-9F, slots 28 are formed diametrically opposite one another, separated by 180 degrees around the head 24. This is necessary to allow both protrusions 98 to slide in the same plane, resulting in an assembly that allows the elongate shaft 22 to pivot relative to the tulip 14 in one plane only. FIG. 9C shows a longitudinal sectional view of assembly 10 taken along line 9C-9C of FIG. 9A. FIGS. 9A-9C illustrate the assembly 10 where the fastener 12 is aligned with the longitudinal axis L-L of the assembly 10 and tulip 14. FIG. 9D shows the longitudinal sectional view of FIG. 9C, but after uniplanar pivoting of fastener 12/shaft 22 relative to tulip 14 by an angle 36 (as shown by the angle 36 between the longitudinal axis L'-L' of the fastener 12 and the longitudinal axis L-L of the tulip 14.

Saddle 16 is configured and dimensioned to be fixed relative to tulip 14 while abutting the proximal portion of head 24 as shown in FIG. 9C. Saddle 16 has a concave distal surface 16S configured and dimensioned as a bearing surface to allow the convex curvature of head 24 to slide relative thereto. Accordingly, as shaft 22 is pivoted relative to tulip 14, head 24 rotates against bearing surfaces of the tulip 14 and saddle 16, as illustrated in FIG. 9D. FIG. 9D illustrates a maximum angle 36 of pivoting, as protrusions 98 make contact with the ends of slots 208, respectively. As shown in FIG. 9E (enlarged view of the portion of FIG. 9C identified within circle 9E), protrusions 98 are centered in slots 208 when shaft 22 is aligned with the longitudinal axis L-L of the tulip 14. Alternatively, slots 108 could be asymmetrically formed so as to allow angulation 36 on one side of the longitudinal axis L-L to be greater than angulation on the other side (angulation in the opposite direction).

In the embodiment shown, saddle 16 is configured and dimensioned to be retained by shoulder 14S when fitted into tulip 14, see FIGS. 9E and 9H. The saddle-shaped tulip 14 further includes a slot 14ST passing therethrough, as shown in FIGS. 9A and 9H that is configured and dimensioned to receive an orthopedic rod or plate therein, in manners known in the art. Threading 14X allows a set screw (not shown) or the like to be torqued against the rod/plate to fix it relative to the tulip 14. The saddle 16 is configured to apply compression to the head 24 to lock an orientation of the fastener 12 relative to the tulip 14, thereby even preventing the movement in the one plane that is otherwise allowed, and thus preventing movement in all planes.

All components 12, 14 and 16 of assembly 10 are preferably made of titanium. Alternatively, one or more components may be made of an alternative material, like previous embodiments described. The uniplanar angulation of assembly 10 may vary, but preferably has a range of about 80 degrees (twice angle 36). The dimensions of the components will vary depending upon the location of the spine in which they are used, the size of the patient (e.g., pediatric vs. adult, male vs. female, etc.), etc. The outside diameter of tulip 14 typically falls within a range of about 8 mm to about 15 mm. The outside diameter of shaft 22 typically falls within a range of about 3 mm to about 8.5 mm. The length of shaft 22 typically falls within a range of about 10 mm to about 100 mm. The height 18H of insert 18 is about 1 mm to about 2 mm, typically about 1.5 mm. The length 18L: of insert 18 is about 1.5 mm to about 3 mm, typically about 2.25 mm.

FIG. 11A is a plan view of a uniplanar surgical screw assembly 10, according to another embodiment of the present invention. FIG. 11B shows assembly 10 having been rotated about its longitudinal axis L-L by ninety degrees, relative to the view shown in FIG. 11A. The assembly 10 of the embodiment of FIGS. 11A-11IJ includes a fastener 12 (see the isolated view of FIG. 11I), a saddle-shaped tulip 14 (see the isolated view of FIG. 11G), and a saddle 16 (see the isolated view of FIG. 11H).

Fastener 12 includes an elongate shaft 22 having a proximal end and a distal end and a head 24 at the proximal end thereof. As shown, elongate shaft 22 is a screw shaft having threads 26 therealong. Head 24 includes a pair of opposing flats 68 on an otherwise convex surface, typically an otherwise spherical surface. The surfaces of flats 68 are substantially parallel to one another as shown in FIG. 11F.

The tulip 14 has a bore 32 therethrough that is dimensioned to allow the distal end of elongate shaft 12 to pass therethrough, but the cross-sectional dimension of the distal opening 32D is smaller than the largest cross-sectional dimension of the head 24, and thereby prevents passage of the head 24 therethrough, as illustrated in FIGS. 11A-11E. Saddle 16 includes a pair of opposing flats 158 (see FIG. 11H) that interface with flats 68 (see FIG. 11F). Saddle 16 is rotationally fixed relative to tulip 14 when assembly 10 is assembled (see FIG. 11E). The interface between flats 158 and flats 68, combined with the prevention of saddle 16 from rotating relative to tulip 14, prevents all pivoting of the shaft 22 relative to the tulip 14, except for in one plane, that plane being parallel to the flats 68 and flats 158.

FIG. 11C shows a longitudinal sectional view of assembly 10 taken along line 11C-11C of FIG. 11B. FIGS. 11A-11C illustrate the assembly 10 where the fastener 12 is aligned with the longitudinal axis L-L of the assembly 10 and tulip 14. FIG. 11D shows the assembly 10 after uniplanar pivoting of fastener 12/shaft 22 relative to tulip 14 by an angle 36 (as shown by the angle 36 between the longitudinal axis L'-L' of the fastener 12 and the longitudinal axis L-L of the tulip 14.

Saddle 16 is configured and dimensioned to be fixed relative to tulip 14 while abutting the proximal portion of head 24 as shown in FIG. 11E. Saddle 16 has a concave distal surface 16s configured and dimensioned as a bearing surface to allow the convex curvature of head 24 to slide relative thereto. Accordingly, as shaft 22 is pivoted relative to tulip 14, head 24 rotates against bearing surfaces of the tulip 14 and saddle 16, as illustrated in FIG. 11D. FIG. 11D illustrates a maximum angle 36 of pivoting. The limits of pivoting are established by the shaft 22 contacting against the tulip 14.

Figure 10:
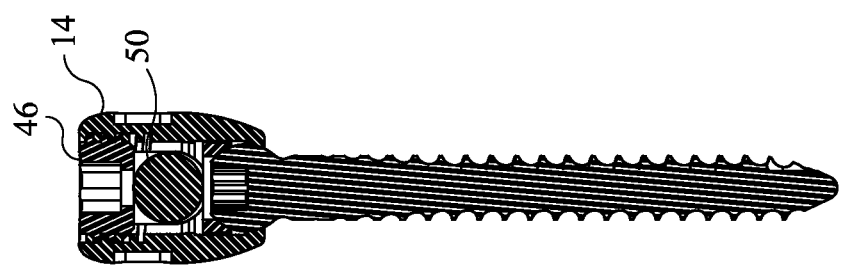
FIG. 10 is a longitudinal sectional view of an assembly locked to a rod according to an embodiment of the present invention.

In the embodiment shown, the saddle-shaped tulip 14 includes a slot 14ST passing therethrough, as shown in FIGS. 11A and 11C that is configured and dimensioned to receive an orthopedic rod or plate therein, in manners known in the art (an example of which is shown in FIG. 10). Threading 14X allows a set screw 46 (see FIG. 10) or the like to be torqued against the rod/plate to fix it relative to the tulip 14.

All components 12, 14 and 16 of assembly 10 are preferably made of titanium. One or more components may be made of an alternative material such as described above. The uniplanar angulation of assembly 10 may vary, but preferably has a range of about 80 degrees (twice angle 36). The dimensions of the components will vary depending upon the location of the spine in which they are used, the size of the patient (e.g., pediatric vs. adult, male vs. female, etc.), etc. The outside diameter of tulip 14 typically falls within a range of about 8 mm to about 15 mm. The outside diameter of shaft 22 typically falls within a range of about 3 mm to about 8.5 mm. The length of shaft 22 typically falls within a range of about 10 mm to about 100 mm. The length of flat 158 is about 4.5 mm to about 6.5 mm, typically about 5.0 mm.

FIG. 11J is a proximal end view of the assembly of FIG. 11B illustrating a tool interface 16T that can be interfaced by a tool to drive the fastener 12 into the bone. The present invention is not limited to this type of interface as any other equivalent type of torquing interface could be used.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A uniplanar surgical screw assembly comprising:
 a fastener including an elongate shaft having a proximal end and a distal end and a head at said proximal end, said head having an external surface;
 a saddle-shaped tulip having a tulip proximal end, a tulip distal end, an external surface and an internal bearing surface, said tulip distal end having a bore therethrough dimensioned to allow said distal end of said elongate shaft to pass therethrough, but to prevent passage of said head therethrough;

a slot formed in one of said external surface of said head or said internal bearing surface of said tulip, said slot having a width dimension and a length dimension greater than said width dimension, wherein said length dimension extends in a proximal-distal direction of said head or said tulip and wherein said slot is bounded in said proximal-distal direction by proximal and distal ends of said slot, respectively; and a protrusion extending from the other of said external surface of said head or said internal bearing surface of said tulip, said protrusion being configured and dimensioned to be received within said slot and to slide in said slot, relative to said slot;

wherein said slot and said protrusion permit said fastener to move relative to said tulip in only one plane; and wherein said proximal and distal ends of said slot limit movement of said fastener relative to said tulip in said proximal-distal direction, upon respective contact with said protrusion.

2. The assembly of claim 1, wherein said slot is formed in said external surface of said head.

3. The assembly of claim 1, wherein said protrusion comprises an insert fitted in a recess in said internal bearing surface of said tulip.

4. The assembly of claim 1, wherein said slot is formed in said internal bearing surface of said tulip.

5. The assembly of claim 4, wherein said protrusion is fixed relative to said head.

6. The assembly of claim 5, wherein said protrusion is integral with said head.

7. The assembly of claim 1, wherein said slot comprises a pair of slots aligned diametrically opposite one another in one of said external surface of said head or said internal bearing surface of said tulip, each said slot extending in a proximal-distal direction; and said protrusion comprises a pair of protrusions extending from the other of said external surface of said head or said internal bearing surface of said tulip, said protrusions being configured and dimensioned to be received within said slots and to slide in said slots, relative to said slots, respectively.

8. The assembly of claim 1, further comprising a saddle, said saddle being configured and dimensioned to be fitted in said tulip against said head of said fastener to prevent said head from moving proximally relative to said tulip.

9. The assembly of claim 8, wherein said saddle is configured to apply compression to said head to lock an orientation of said fastener relative to said tulip, thereby preventing said movement in one plane.

10. A uniplanar surgical screw assembly comprising:
a fastener including an elongate shaft having a proximal end and a distal end and a head at said proximal end, said head having a flat surface formed on an external surface having otherwise substantially spherical curvature;

a saddle-shaped tulip having a tulip proximal end, a tulip distal end, an external surface and an internal bearing surface having substantially spherical curvature configured to permit articulation of a curved portion of said external surface of said head thereagainst, and said tulip distal end having a bore therethrough dimensioned to allow said distal end of said elongate shaft to pass therethrough, but to prevent passage of said head therethrough; and an interface component having a flat interface surface;

wherein said saddle-shaped tulip comprises a recess formed in said internal bearing surface;

wherein said interface component comprises an insert having said flat interface surface and a non-flat surface opposite said flat interface surface, said non-flat surface configured and dimensioned to be received in said recess;

wherein said non-flat surface has a least first and second curved portions, said first curved portion having a first radius of curvature, and said second curved portion having a second radius of curvature, wherein said second radius of curvature is greater than said first radius of curvature; and wherein, when said assembly is assembled, said flat interface surface interfaces with said flat surface of said head, thereby permitting said fastener to move relative to said tulip in only one plane.

11. The assembly of claim 10, wherein said flat surface on said head comprises a pair of said flat surfaces formed diametrically opposite one another on said head; and wherein said flat interface surface comprises a pair of said flat interface surfaces configured to interface with said pair of said flat surfaces, respectively.

12. The assembly of claim 10, further comprising a saddle, said saddle being configured and dimensioned to be fitted in said tulip against said head of said fastener to prevent said head from moving proximally relative to said tulip.

13. The assembly of claim 12, wherein said saddle is configured to apply compression to said head to lock an orientation of said fastener relative to said tulip, thereby preventing said movement in one plane.

14. The assembly of claim 10, wherein when said insert is received in said recess and said head is received in said tulip, said flat interface surface of said insert interfaces with said flat surface of said head, thereby permitting said fastener to move relative to said tulip in only one plane.

15. The assembly of claim 10, wherein said recess comprises a pair of recesses formed in said internal bearing surface at diametrically opposite locations; and wherein said insert comprises a pair of said inserts configured and dimensioned to be received in said recesses, respectively.

16. The assembly of claim 15, further comprising a saddle, said saddle being configured and dimensioned to be fitted in said tulip against said head of said fastener to prevent said head from moving proximally relative to said tulip.

17. The assembly of claim 16, wherein said saddle is configured to apply compression to said head to lock an orientation of said fastener relative to said tulip, thereby preventing said movement in one plane.

18. The assembly of claim 10, wherein said non-flat surface comprises a bulbous portion extending further from said flat side than an extent to which a remainder of said non-flat side extends from said flat side.

19. The assembly of claim 10, wherein said non-flat surface comprises a proximal end portion, a central portion, and a distal end portion, wherein said central portion extends further from said flat interface surface than the distances by which said proximal and distal end portions extend from said flat interface surface side.

20. The assembly of claim 10, wherein said non-flat surface comprises a proximal end portion, a central portion, and a distal end portion, wherein said central portion has a first curvature and said proximal and distal end portions have a second curvature, said first curvature having a smaller radius of curvature than said second curvature.

21. A uniplanar surgical screw assembly comprising:
   a fastener including an elongate shaft having a proximal end and a distal end and a head at said proximal end, said head having an external surface;
   a saddle-shaped tulip having a tulip proximal end, a tulip distal end, an external surface and an internal bearing surface configured to contact said external surface of said head, said tulip distal end having a bore therethrough dimensioned to allow said distal end of said elongate shaft to pass therethrough, but to prevent passage of said head therethrough;
   a saddle, said saddle being configured and dimensioned to be fitted in said tulip against said head of said fastener to prevent said head from moving proximally relative to said tulip, said saddle having an internal surface configured to interface with said external surface of said head;
   a slot formed in one of said external surface of said head or said internal surface of said saddle and extending in a proximal-distal direction; and
   a protrusion extending from the other of said external surface of said head or said internal surface of said saddle, said protrusion being configured and dimensioned to be received within said slot and to slide in said slot, relative to said slot;
   wherein said slot and said protrusion permit said fastener to move relative to said tulip in only one plane.

22. The assembly of claim 21, wherein said protrusion extends from said internal surface of said saddle.

23. The assembly of claim 22, wherein said protrusion is integrally formed with said internal surface of said saddle.

24. The assembly of claim 21, wherein said slot is formed in said external surface of said head.

25. The assembly of claim 21, wherein said protrusion is fixed relative to said saddle.

26. The assembly of claim 21, wherein said slot comprises a pair of slots aligned diametrically opposite one another in one of said external surface of said head or said internal surface of said saddle, each said slot extending in said proximal-distal direction; and
   said protrusion comprises a pair of protrusions extending from the other of said external surface of said head or said internal surface of said saddle, said protrusions being configured and dimensioned to be received within said slots and to slide in said slots, relative to said slots, respectively.

27. The assembly of claim 21, wherein said saddle and said tulip are configured to contact and apply compression to said head to lock an orientation of said fastener relative to said tulip, thereby preventing said movement in one plane.

28. A uniplanar surgical screw assembly comprising:
   a fastener including an elongate shaft having a proximal end and a distal end and a head at said proximal end, said head having an external surface;
   a saddle-shaped tulip having a tulip proximal end, a tulip distal end, an external surface and an internal bearing surface, said tulip distal end having a bore therethrough dimensioned to allow said distal end of said elongate shaft to pass therethrough, but to prevent passage of said head therethrough;
   a saddle, said saddle being configured and dimensioned to be fitted in said tulip against said head of said fastener to prevent said head from moving proximally relative to said tulip, and
   a protrusion extending from the said head,
   wherein said saddle includes a notch configured to allow translation of said protrusion;
   wherein said notch and said protrusion permit said fastener to move relative to said tulip in only one plane.

29. The assembly of claim 10, wherein said non-flat surface is shaped and configured to prevent said insert from sliding relative to said recess.

\* \* \* \* \*